(12) United States Patent
Xiao et al.

(10) Patent No.: US 10,308,705 B2
(45) Date of Patent: Jun. 4, 2019

(54) OPTIMIZED HUMAN CLOTTING FACTOR VIII GENE EXPRESSION CASSETTES AND THEIR USE

(71) Applicant: The University of North Carolina at Chapel Hill, Chapel Hill, NC (US)

(72) Inventors: Xiao Xiao, Chapel Hill, NC (US); Juan Li, Chapel Hill, NC (US); Zhenhua Yuan, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 187 days.

(21) Appl. No.: 15/017,015

(22) Filed: Feb. 5, 2016

(65) Prior Publication Data

US 2016/0229904 A1  Aug. 11, 2016

Related U.S. Application Data

(60) Provisional application No. 62/112,901, filed on Feb. 6, 2015.

(51) Int. Cl.
*C07K 14/755* (2006.01)
*C12N 15/63* (2006.01)
*A61K 38/00* (2006.01)

(52) U.S. Cl.
CPC .......... *C07K 14/755* (2013.01); *C12N 15/63* (2013.01); *A61K 38/00* (2013.01)

(58) Field of Classification Search
CPC .................................................. C12N 14/755
See application file for complete search history.

(56) References Cited

U.S. PATENT DOCUMENTS

2008/0227691 A1  9/2008 Ostergaard et al.

FOREIGN PATENT DOCUMENTS

| WO | WO 2011/097456 A2 | 8/2011 |
|---|---|---|
| WO | WO 2013/057167 A1 | 4/2013 |
| WO | 2014/064277 A1 | 5/2014 |
| WO | 2014/127215 A1 | 8/2014 |

OTHER PUBLICATIONS

NPL-PDF Blast SEQ ID No. 1, p. 1-4, 2018 (Year: 2018).*
NPL-PDF Blast SEQ ID No. 2, p. 1-11, 2018 (Year: 2018).*
NPL-PDF Blast SEQ ID No. 3, p. 1-14, 2018 (Year: 2018).*
NPL-PDF Blast SEQ ID No. 4, p. 1-18, 2018 (Year: 2018).*
Notification Concerning Transmittal of International Preliminary Report on Patentability corresponding to International Application No. PCT/US2016/016777 dated Aug. 17, 2017.
McIntosh et al. "Therapeutic levels of FVIII following a single peripheral vein administration of rAAV vector encoding a novel human factor VII variant", bloodjournal.hematologylibrary.org p. 44 (2013).
Notification of Transmittal of the International Search Report and the Written Opinion of the International Searching Authority, or the Declaration corresponding to International Application No. PCT/US2016/016777 dated May 19, 2016.
Extended European Search Report corresponding to European Application No. 16747334.7 dated Sep. 14, 2018.
Partial Supplementary European Search Report corresponding to European Application No. 16747334.7 dated Jun. 4, 2018.

\* cited by examiner

*Primary Examiner* — Anoop K Singh
*Assistant Examiner* — Magdalene K Sgagias
(74) *Attorney, Agent, or Firm* — Myers Bigel, P.A.

(57) ABSTRACT

The invention relates to synthetic liver-specific promoters and expression constructs for producing polypeptides and functional nucleic acids in the liver of a subject. The invention further relates to Factor VIII proteins containing modifications in the amino acid sequence of the Factor VIII protein, as well as nucleic acid constructs encoding the Factor VIII proteins and methods of using these compositions to treat a bleeding disorder.

16 Claims, 7 Drawing Sheets

Specification includes a Sequence Listing.

CTGTTTACTCTGGTTAATTTTTAAAGGAGGGTAAACAGTGCCTGAAAG
　HNF3　　　　HNF1　　　　　　HNF3

CTGACCTTTGCCCACATTCCTCCGGTAGACATTAACTTATTAAATT
　HNF4A　　　　TEF

GATTCTGATTACAAATCTGACCTTTGCCCCCATCTCACCCAGTAACAATGCAA
　CEBPA　　　　　HNF4A

GAGTTGATGTCAGTCTATAAAAAGCGAAGCGCGCGGTGGGCGGGGTTCGCTGC
　　　AP1　　　TATA　　　　　　　　　　　SP1

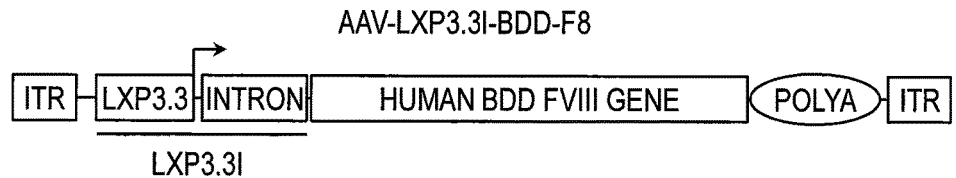

LXP3.3I (UNDERLINED IS VH4 INTRON SEQUENCE):
CTGTTTACTCTGGTTAATTTTTAAAGGAGGGTAAACAGTGCCTGAAAGCTGA
CCTTTGCCCACATTCCTCCGGTAGACATTAACTTATTAAATTGATTCTGATTA
CAAATCTGACCTTTGCCCCCATCTCACCCAGTAACAATGCAAGAGTTGATG
TCAGTCTATAAAAAGCGAAGCGCGCGGTGGGCGGGGTTCGCTGCCTGCA
GGTGAGTATCTCAGGGATCCAGACATGGGGATATGGGAGGTGCCTCTGAT
CCCAGGGCTCACTGTGGGTCTCTCTGTTCACAG

*FIG. 4*

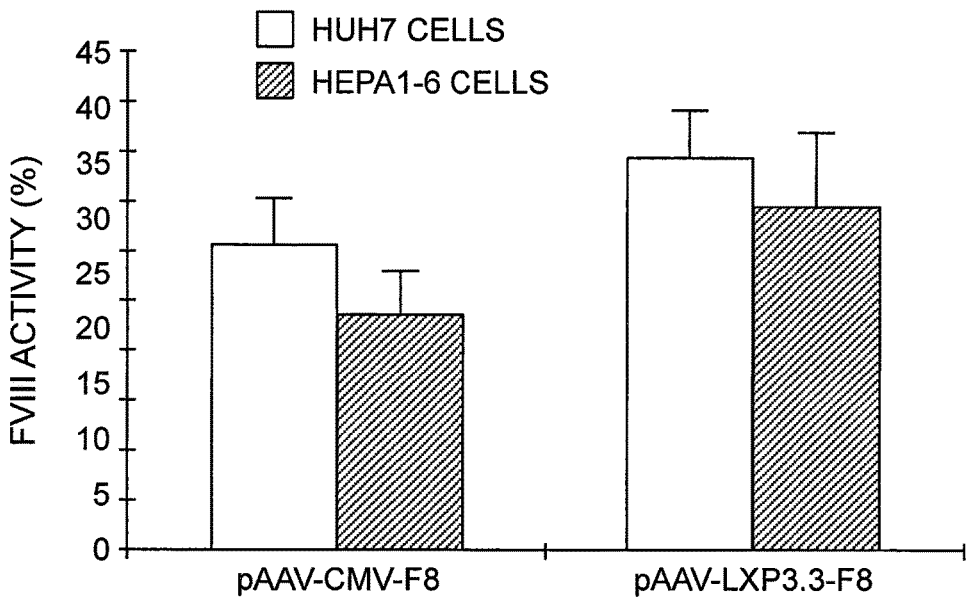

*FIG. 5*

SEQUENCE LISTING

<160> NUMBER OF SEQ ID NOS: 34

<210> SEQ ID NO 1
<211> LENGTH: 200
<212> TYPE: DNA
<213> ORGANISM: Homo sapiens

<400> SEQUENCE: 1
ctgtttactc tggttaattt ttaaaggagg gtaaacagtg cctgaaagct gacctttgcc      60
cacattcctc cggtagacat taacttatta aattgattct gattacaaat ctgacctttg     120
cccccatctc acccagtaac aatgcaagag ttgatgtcag tctataaaaa gcgaagcgcg     180
cggtgggcgg ggttcgctgc                                                 200

<210> SEQ ID NO 2
<211> LENGTH: 288
<212> TYPE: DNA
<213> ORGANISM: Artificial
<220> FEATURE:
<223> OTHER INFORMATION: LXP3.3I synthetic promoter sequence

<400> SEQUENCE: 2
ctgtttactc tggttaattt ttaaaggagg gtaaacagtg cctgaaagct gacctttgcc      60
cacattcctc cggtagacat taacttatta aattgattct gattacaaat ctgacctttg     120
cccccatctc acccagtaac aatgcaagag ttgatgtcag tctataaaaa gcgaagcgcg     180
cggtgggcgg ggttcgctgc ctgcaggtga gtatctcagg gatccagaca tgggggatatg     240 ggaggtgcct ctgatcccag ggctcactgt gggtctctct gttcacag                  288

<210> SEQ ID NO 3
<211> LENGTH: 4374
<212> TYPE: DNA
<213> ORGANISM: Artificial
<220> FEATURE:
<223> OTHER INFORMATION: Synthetic human B-domain deleted factor FVIII
      coding sequence

<400> SEQUENCE: 3
atgcagatcg agctgtctac ctgcttcttc ctgtgcctgc tgcggttctg cttcagcgcc      60
accagacggt actatctggg cgccgtggaa ctgagctggg actacatgca gagcgacctg     120
ggcgagctgc ccgtggatgc cagattccct ccaagagtgc caagagcttt cccttcaac      180 acctccgtgg tgtacaagaa aaccctgttc gtggaattca ccgaccacct gttcaatatc     240
gccaagccca accccctg gatgggcctg ctgggaccta caattcaggc cgaggtgtac      300
gacaccgtcg tgatcaccct gaagaacatg gccagccacc ccgtgtctct gcatgccgtg     360
ggagtgtcct actggaaggc ctctgagggc gccgagtacg acgatcagac cagccagcgc     420
gagaaagagg acgacaaggt gttccctggc ggcagccaca cctacgtgtg gcaggtgctg     480
aaagaaaacg gccccatggc ctccgaccct ctgtgcctga tatacagcta cctgagccac     540
gtggacctcg tgaaggacct gaacagcggc ctgatcggag ccctgctcgt gtgtagagag     600
ggcagcctgg ccaaagagaa aacccagacc tgcacaagt tcatcctgct gttcgccgtg     660
ttcgacgagg caagagctg gcacagcgag acaaagaaca gcctgatgca ggaccgggac     720
gccgcctctg ctagagcctg gcccaaaatg cacaccgtga acggctacgt gaacagaagc     780
ctgcccggac tgatcggctg caccggaag tctgtgtact ggcacgtgat cggcatgggc     840
accacccctg aggtgcacag catctttctg gaaggacaca ccttctctcgt gcggaaccac     900

```
cggcaggcca gcctggaaat cagccctatc accttcctga ccgcccagac actgctgatg    960
gacctgggcc agtttctgct gttctgccac atcagctccc accagcacga cggcatggaa   1020
gcctacgtga aggtggacag ctgccccgag gaaccccagc tgcggatgaa gaacaacgag   1080
gaagccgagg actacgacga cgacctgacc gacagcgaga tggacgtggt gcgcttcgac   1140
gacgataaca gccccagctt catccagatc agaagcgtgg ccaagaagca ccccaagacc   1200
tgggtgcact atatcgccgc cgaggaagag gactgggatt acgccctctc tggtgctggcc  1260 cccgacgaca gaagctacaa gagccagtac ctgaacaatg gccccagcg gatcggccgg   1320 aagtataaga agtgcggtt catggcctac accgacgaga cattcaagac cagagaggcc    1380
atccagcacg agagcggcat cctgggccct ctgctgtatg gcgaagtggg cgacaccctg   1440
ctgatcatct tcaagaacca ggccagcaga ccctacaaca tctaccctca cggcatcacc   1500
gacgtgcggc ccctgtactc tagaaggctg cccaagggcg tgaaacacct gaaggacttc   1560
cccatcctgc ccggcgagat tttcaagtac aagtggaccg tgaccgtgga agatggcccc   1620
accaagagcg accccagatg cctgacacgg tactacagca gcttcgtgaa catggaacgg   1680
gacctggcct ccggcctgat tgcccactg ctgatctgct acaaagaaag cgtggaccag   1740
cggggcaacc agatcatgag cgacaagcgg aacgtgatcc tgtttagcgt gttcgatgag   1800
aaccggtcct ggtatctgac cgagaatatc cagcggttcc tgcccaaccc tgccggcgtg   1860
cagctggaag atcctgagtt ccaggcctcc aacatcatgc actccatcaa tggctatgtg   1920
ttcgacagcc tgcagctgag cgtgtgcctg cacgaggtgg cctactggta catcctgagc   1980 atcgggccc agaccgactt cctgtccgtg ttcttctccg gctacacctt caagcacaag   2040
atggtgtacg aggatacct gaccctgttc ccctttagcg gcgaaaccgt gttcatgagc   2100
atggaaaacc ccggcctgtg gatcctgggc tgccacaaca gcgacttccg gaacagaggc   2160
atgaccgccc tgctgaaggt gtccagctgc gacaagaaca ccggcgacta ctacgaggac   2220
agctatgagg acatcagcgc ctacctgctg agcaagaaca atgccatcga gcccagaagc   2280
ttcagccagc ccctgtgctg aagcggcac cagagagaga tcacccggac caccctgcag   2340
tccgaccagg aagagatcga ttacgacgac accatcagcg tggaaatgaa gaaagaagat   2400
ttcgacatct acgacgagga cgagaaccag agcccccggt cctttcagaa aaagacccgg   2460
cactacttca ttgccgctgt ggaacggctg tgggactacg gcatgagcag cagccctcac   2520
gtgctgagaa acagggccca gagcggcagc gtgcccagt tcaagaaagt ggtgttccag   2580
gaattcacag acggcagctt tacccagcct ctgtaccgcg cgagctgaa cgaacacctg   2640 ggactgctgg cccctatat ccgggccgaa gtggaagata acatcatggt caccttccgg   2700
aatcaggcct cccggcccta cagcttctac agctccctga tcagctacga agaggaccag   2760
agacagggcg ctgagccccg aagaacttc gtgaagccca acgagactaa gacctacttt   2820
tggaaggtgc agcaccacat ggcccctaca aaggacgagt tcgactgcaa ggcctgggcc   2880
tacttctccg atgtggacct ggaaaaggac gtgcactctg ggctgatcgg cccctgctc    2940 gtgtgccaca ccaacaccct gaatcccgcc cacggcagac aagtgacagt gcaggaattc   3000
gccctgttct tcaccatctt cgacgaaaca aagagctggt acttcaccga aacatggaa    3060 agaaactgcc gggctccctg caacatccag atggaagatc ccaccttcaa agagaactac   3120
cggttccacg ccatcaacgg ctacatcatg gacacactgc ccggcctcgt gatggctcag   3180
gatcagcgga tccggtggta tctgctgtcc atgggctcca acgagaacat ccacagcatc   3240
cacttcagcg gccacgtgtt caccgtgcgg aaaaaagaag agtacaaaat ggcccctgtac  3300
```

```
aacctgtacc ctggggtgtt cgagacagtg gaaatgctgc ccagcaaggc cggcatctgg    3360
cgggtggaat gtctgatcgg cgagcatctg cacgctggga tgagcacact gtttctggtg    3420
tacagcaaca agtgccagac acctctgggc atggcctctg ccacatccg ggactttcag     3480 atcacagcca gcggccagta tggccagtgg gccccaaaac tggccagact gcactacagc    3540
ggcagcatca acgcctggtc caccaaagag cccttcagct ggatcaaggt ggacctgctg    3600
gctcccatga tcatccacgg aatcaagacc cagggcgcca gacagaagtt ctccagcctg    3660
tacatctccc agttcatcat catgtactcc ctggacggca agaagtggca gacctaccgg    3720
ggcaatagca ccggcaccct gatggtgttc ttcggcaacg tggactccag cggcattaag    3780
cacaacatct tcaaccccc catcattgcc cggtacatcc ggctgcaccc cacccactac    3840
agcatccggt ccaccctgag aatggaactg atgggctgcg acctgaactc ctgcagcatg    3900
cccctgggga tggaaagcaa ggccatctcc gacgcccaga tcaccgcctc cagctacttc    3960
accaacatgt tcgccacctg gtccccatcc aaggcccggc tgcatctgca gggcagaagc    4020
aatgcttgga ggccccaagt gaacaacccc aaagaatggc tgcaggtgga cttccagaaa    4080
accatgaaag tgaccggcgt gaccacccag ggcgtgaagt ctctgctgac ctctatgtac    4140
gtgaaagagt tcctgatctc cagcagccag gacggccacc agtggaccct gttttccag    4200 aacggcaaag tgaaagtgtt tcaggggaac caggacagct tcacccccgt cgtgaatagc    4260
ctggaccctc cactgctgac cagatacctg cggatccacc ctcagagttg ggtgcaccag    4320
attgctctgc ggatggaagt gctgggatgc gaggcccagg acctgtactg ataa          4374

<210> SEQ ID NO 4
<211> LENGTH: 5045
<212> TYPE: DNA
<213> ORGANISM: Artificial
<220> FEATURE:
<223> OTHER INFORMATION: Recombinant AAV vector sequence

<400> SEQUENCE: 4
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg      120
gccaactcca tcactagggg ttcctagatc tacgcgtctg tttactctgg ttaattttta     180
aaggagggta acagtgcct gaaagctgac ctttgcccac attcctccgg tagacattaa      240
cttattaaat tgattctgat tacaaatctg acctttgccc ccatctcacc cagtaacaat     300
gcaagagttg atgtcagtct ataaaaagcg aagcgcgcgg tgggcggggt tcgctgcctg    360
caggtgagta tctcagggat ccagacatgg ggatatggga ggtgcctctg atcccagggc    420
tcactgtggg tctctctgtt cacagcctgc tagcgccacc atgcagatcg agctgtctac    480
ctgcttcttc ctgtgcctgc tgcggttctg cttcagcgcc accagacggt actatctggg    540
cgccgtggaa ctgagctggg actacatgca gagcgacctg ggcgagctgc ccgtggatgc    600
cagattccct ccaagagtgc ccaagagctt ccccttcaac acctccgtgg tgtacaagaa    660
aaccctgttc gtggaattca ccgaccacct gttcaatatc gccaagccca gaccccctg     720 gatgggcctg ctgggaccta caattcaggc cgaggtgtac gacaccgtcg tgatcacct    780 gaagaacatg gccagccacc ccgtgtctct gcatgccgtg ggagtgtcct actggaaggc   840
ctctgagggc gccgagtacg acgatcagac cagccagcgc gagaaagagg acgacaaggt   900
gttccctggc ggcagccaca cctacgtgtg gcaggtgctg aaagaaaacg gccccatggc   960
```

-continued

```
ctccgaccct ctgtgcctga catacagcta cctgagccac gtggacctcg tgaaggacct    1020
gaacagcggc ctgatcggag ccctgctcgt gtgtagagag ggcagcctgg ccaaagagaa    1080
aacccagacc ctgcacaagt tcatcctgct gttcgccgtg ttcgacgagg caagagctg     1140
gcacagcgag acaaagaaca gcctgatgca ggaccgggac gccgcctctg ctagagcctg    1200
gcccaaaatg cacaccgtga acggctacgt gaacagaagc ctgcccggac tgatcggctg    1260
ccaccggaag tctgtgtact ggcacgtgat cggcatgggc accacccctg aggtgcacag    1320
catctttctg gaaggacaca cctttctcgt gcggaaccac cggcaggcca gcctggaaat    1380
cagccctatc accttcctga ccgcccagac actgctgatg gacctgggcc agtttctgct    1440
gttctgccac atcagctccc accagcacga cggcatggaa gcctacgtga aggtggacag    1500
ctgccccgag aaccccagc tgcggatgaa gaacaacgag gaagccgagg actacgacga    1560
cgacctgacc gacagcgaga tggacgtggt gcgcttcgac gacgataaca gccccagctt    1620
catccagatc agaagcgtgg ccaagaagca ccccaagacc tgggtgcact atatcgccgc    1680
cgaggaagag gactgggatt acgcccctct ggtgctggcc cccgacgaca gaagctacaa    1740
gagccagtac ctgaacaatg ccccccagcg gatcggccgg aagtataaga agtgcggtt    1800
catggcctac accgacgaga cattcaagac cagagaggcc atccagcacg agagcggcat    1860
cctgggccct ctgctgtatg gcgaagtggg cgacaccctg ctgatcatct tcaagaacca    1920
ggccagcaga ccctacaaca tctaccctca cggcatcacc gacgtgcggc cctgtactc    1980
tagaaggctg cccaagggcg tgaaacacct gaaggacttc cccatcctgc ccggcgagat    2040
tttcaagtac aagtgaccg tgaccgtgga agatggcccc accaagagcg accccagatg    2100
cctgacacgg tactacagca gcttcgtgaa catggaacgg gacctggcct ccggcctgat    2160
tggcccactg ctgatctgct acaaagaaag cgtggaccag cggggcaacc agatcatgag    2220
cgacaagcgg aacgtgatcc tgtttagcgt gttcgatgag aaccggtcct ggtatctgac    2280
cgagaatatc cagcggttcc tgcccaaccc tgccggcgtg cagctggaag atcctgagtt    2340
ccaggcctcc aacatcatgc actccatcaa tggctatgtg ttcgacagcc tgcagctgag    2400
cgtgtgcctg cacgaggtgg cctactggta catcctgagc atcggggccc agaccgactt    2460
cctgtccgtg ttcttctccg gctacacctt caagcacaag atggtgtacg aggatacct     2520
gaccctgttc cccttagcg gcgaaaccgt gttcatgagc atggaaaacc ccggcctgtg    2580
gatcctgggc tgccacaaca gcgacttccg gaacagaggc atgaccgccc tgctgaaggt    2640
gtccagctgc gacaagaaca ccggcgacta ctacgaggac agctatgagg acatcagcgc    2700
ctacctgctg agcaagaaca atgccatcga gcccagaagc ttcagccagc ccctgtgct     2760
gaagcggcac cagagagaga tcacccggac caccctgcag tccgaccagg aagagatcga    2820
ttacgacgac accatcagcg tggaaatgaa gaaagaagat ttcgacatct acgacgagga    2880
cgagaaccag agcccccggt cctttcagaa aaagacccgg cactacttca ttgccgctgt    2940
ggaacggctg tgggactacg gcatgagcag cagccctcac gtgctgagaa cagggccca    3000
gagcggcagc gtgccccagt tcaagaaagt ggtgttccag gaattcacag acggcagctt    3060
tacccagcct ctgtaccgcg cgagctgaa cgaacacctg ggactgctgg cccctatat     3120
ccgggccgaa gtggaagata acatcatggt caccttccgg aatcaggcct cccggcccta    3180
cagcttctac agctccctga tcagctacga gaggaccag agacagggcg ctgagccccg    3240
gaagaacttc gtgaagccca acgagactaa gacctacttt tggaaggtgc agcaccacat    3300
ggccctaca aaggacgagt tcgactgcaa ggcctgggcc tacttctccg atgtggacct    3360
```

-continued

```
ggaaaaggac gtgcactctg ggctgatcgg cccctgctc gtgtgccaca ccaacaccct    3420
gaatcccgcc cacggcagac aagtgacagt gcaggaattc gccctgttct tcaccatctt    3480
cgacgaaaca aagagctggt acttcaccga aacatggaa agaaactgcc gggctccctg     3540
caacatccag atgaagatc ccaccttcaa agagaactac cggttccacg ccatcaacgg     3600
ctacatcatg gacacactgc ccggcctcgt gatggctcag gatcagcgga tccggtggta    3660
tctgctgtcc atgggctcca acgagaacat ccacagcatc cacttcagcg ccacgtgtt    3720
caccgtgcgg aaaaagaag agtacaaaat ggccctgtac aacctgtacc tggggtgtt     3780
cgagacagtg gaaatgctgc ccagcaaggc cggcatctgg cgggtggaat gtctgatcgg    3840
cgagcatctg cacgctggga tgagcacact gtttctggtg tacagcaaca agtgccagac    3900
acctctgggc atggcctctg ccacatccg ggactttcag atcacagcca gcggccagta    3960
tggccagtgg gccccaaaac tggccagact gcactacagc ggcagcatca acgcctggtc    4020
caccaaagag cccttcagct ggatcaaggt ggacctgctg ctcccatga tcatccacgg    4080
aatcaagacc cagggcgcca gacagaagtt ctccagcctg tacatctccc agttcatcat    4140
catgtactcc ctggacggca agaagtggca gacctaccgg gcaatagca ccggcaccct    4200
gatggtgttc ttcggcaacg tggactccag cggcattaag cacaacatct tcaacccccc    4260
catcattgcc cggtacatcc ggctgcaccc cacccactac agcatccggt ccaccctgag    4320
aatggaactg atgggctgcg acctgaactc ctgcagcatg cccctgggga tggaaagcaa    4380
ggccatctcc gacgcccaga tcaccgcctc cagctacttc accaacatgt tcgccacctg    4440
gtccccatcc aaggcccggc tgcatctgca gggcagaagc aatgcttgga ggccccaagt    4500
gaacaacccc aaagaatggc tgcaggtgga cttccagaaa accatgaaag tgaccggcgt    4560
gaccacccag ggcgtgaagt ctctgctgac ctctatgtac gtgaaagagt tcctgatctc    4620
cagcagccag gacggccacc agtgaccct gttttccag aacggcaaag tgaaagtgtt    4680
tcagggaaac caggacagct tcacccccgt cgtgaatagc ctggaccctc cactgctgac    4740
cagatacctg cggatccacc ctcagagttg ggtgcaccag attgtctctgc ggatggaagt    4800
gctgggatgc gaggcccagg acctgtactg ataagtcgac aggcctaata aagagctcag    4860
atgcatcgat cagagtgtgt tggttttttg tgtgagatct aggaacccct agtgatggag    4920
ttggccactc cctctctgcg cgctcgctcg ctcactgagg ccgccggc aaagcccggg     4980
cgtcgggcga cctttggtcg cccggcctca gtgagcgagc gagcgcgcag agaggagtg     5040
gccaa                                                              5045
```

<210> SEQ ID NO 5
<211> LENGTH: 2333
<212> TYPE: PRT
<213> ORGANISM: Homo sapiens

<400> SEQUENCE: 5

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Val His Leu Phe Asn Ile Ala Lys Pro
    50                  55                  60
```

```
Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
             85                  90                  95

Ser Leu His Ala Val Gly Val Ser Tyr Trp Lys Ala Ser Glu Gly Ala
        100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
                180                 185                 190

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
        210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
                260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
        290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
                340                 345                 350

Ser Glu Met Asp Val Val Arg Phe Asp Asp Asp Asn Ser Pro Ser Phe
            355                 360                 365

Ile Gln Ile Arg Ser Val Ala Lys Lys His Pro Lys Thr Trp Val His
        370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
        450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
```

-continued

```
                485                 490                 495
His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
                515                 520                 525

Leu Thr Arg Tyr Tyr Ser Ser Phe Val Asn Met Glu Arg Asp Leu Ala
                530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
                595                 600                 605

Gln Ala Ser Asn Ile Met His Ser Ile Asn Gly Tyr Val Phe Asp Ser
                610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
                675                 680                 685

Ile Leu Gly Cys His Asn Ser Asp Phe Arg Asn Arg Gly Met Thr Ala
                690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
                740                 745                 750

Gln Lys Gln Phe Asn Ala Thr Thr Ile Pro Glu Asn Asp Ile Glu Lys
                755                 760                 765

Thr Asp Pro Trp Phe Ala His Arg Thr Pro Met Pro Lys Ile Gln Asn
                770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
                835                 840                 845

Phe Thr Pro Glu Ser Gly Leu Gln Leu Arg Leu Asn Glu Lys Leu Gly
                850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
                900                 905                 910
```

-continued

Tyr Asp Ser Gln Leu Asp Thr Thr Leu Phe Gly Lys Lys Ser Ser Pro
              915                 920                 925

Leu Thr Glu Ser Gly Gly Pro Leu Ser Leu Ser Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
                980                 985                 990

Val Ser Ile Ser Leu Leu Lys Thr Asn Lys Thr Ser Asn Asn Ser Ala
              995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
    1100                1105                1110

Gly Lys Asn Ser Leu Asn Ser Gly Gln Gly Pro Ser Pro Lys Gln
    1115                1120                1125

Leu Val Ser Leu Gly Pro Glu Lys Ser Val Glu Gly Gln Asn Phe
    1130                1135                1140

Leu Ser Glu Lys Asn Lys Val Val Val Gly Lys Gly Glu Phe Thr
    1145                1150                1155

Lys Asp Val Gly Leu Lys Glu Met Val Phe Pro Ser Ser Arg Asn
    1160                1165                1170

Leu Phe Leu Thr Asn Leu Asp Asn Leu His Glu Asn Asn Thr His
    1175                1180                1185

Asn Gln Glu Lys Lys Ile Gln Glu Glu Ile Glu Lys Lys Glu Thr
    1190                1195                1200

Leu Ile Gln Glu Asn Val Val Leu Pro Gln Ile His Thr Val Thr
    1205                1210                1215

Gly Thr Lys Asn Phe Met Lys Asn Leu Phe Leu Leu Ser Thr Arg
    1220                1225                1230

Gln Asn Val Glu Gly Ser Tyr Glu Gly Ala Tyr Ala Pro Val Leu
    1235                1240                1245

Gln Asp Phe Arg Ser Leu Asn Asp Ser Thr Asn Arg Thr Lys Lys
    1250                1255                1260

His Thr Ala His Phe Ser Lys Lys Gly Glu Glu Glu Asn Leu Glu
    1265                1270                1275

Gly Leu Gly Asn Gln Thr Lys Gln Ile Val Glu Lys Tyr Ala Cys
    1280                1285                1290

Thr Thr Arg Ile Ser Pro Asn Thr Ser Gln Gln Asn Phe Val Thr
    1295                1300                1305

-continued

```
Gln Arg Ser Lys Arg Ala Leu Lys Gln Phe Arg Leu Pro Leu Glu
1310                1315                1320

Glu Thr Glu Leu Glu Lys Arg Ile Ile Val Asp Thr Ser Thr
1325                1330                1335

Gln Trp Ser Lys Asn Met Lys His Leu Thr Pro Ser Thr Leu Thr
1340                1345                1350

Gln Ile Asp Tyr Asn Glu Lys Glu Lys Gly Ala Ile Thr Gln Ser
1355                1360                1365

Pro Leu Ser Asp Cys Leu Thr Arg Ser His Ser Ile Pro Gln Ala
1370                1375                1380

Asn Arg Ser Pro Leu Pro Ile Ala Lys Val Ser Ser Phe Pro Ser
1385                1390                1395

Ile Arg Pro Ile Tyr Leu Thr Arg Val Leu Phe Gln Asp Asn Ser
1400                1405                1410

Ser His Leu Pro Ala Ala Ser Tyr Arg Lys Lys Asp Ser Gly Val
1415                1420                1425

Gln Glu Ser Ser His Phe Leu Gln Gly Ala Lys Lys Asn Asn Leu
1430                1435                1440

Ser Leu Ala Ile Leu Thr Leu Glu Met Thr Gly Asp Gln Arg Glu
1445                1450                1455

Val Gly Ser Leu Gly Thr Ser Ala Thr Asn Ser Val Thr Tyr Lys
1460                1465                1470

Lys Val Glu Asn Thr Val Leu Pro Lys Pro Asp Leu Pro Lys Thr
1475                1480                1485

Ser Gly Lys Val Glu Leu Leu Pro Lys Val His Ile Tyr Gln Lys
1490                1495                1500

Asp Leu Phe Pro Thr Glu Thr Ser Asn Gly Ser Pro Gly His Leu
1505                1510                1515

Asp Leu Val Glu Gly Ser Leu Leu Gln Gly Thr Glu Gly Ala Ile
1520                1525                1530

Lys Trp Asn Glu Ala Asn Arg Pro Gly Lys Val Pro Phe Leu Arg
1535                1540                1545

Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
1565                1570                1575

Glu Trp Lys Ser Gln Glu Lys Ser Pro Glu Lys Thr Ala Phe Lys
1580                1585                1590

Lys Lys Asp Thr Ile Leu Ser Leu Asn Ala Cys Glu Ser Asn His
1595                1600                1605

Ala Ile Ala Ala Ile Asn Glu Gly Gln Asn Lys Pro Glu Ile Glu
1610                1615                1620

Val Thr Trp Ala Lys Gln Gly Arg Thr Glu Arg Leu Cys Ser Gln
1625                1630                1635

Asn Pro Pro Val Leu Lys Arg His Gln Arg Glu Ile Thr Arg Thr
1640                1645                1650

Thr Leu Gln Ser Asp Gln Glu Glu Ile Asp Tyr Asp Asp Thr Ile
1655                1660                1665

Ser Val Glu Met Lys Lys Glu Asp Phe Asp Ile Tyr Asp Glu Asp
1670                1675                1680

Glu Asn Gln Ser Pro Arg Ser Phe Gln Lys Lys Thr Arg His Tyr
1685                1690                1695

Phe Ile Ala Ala Val Glu Arg Leu Trp Asp Tyr Gly Met Ser Ser
```

```
                1700                1705                1710

Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe
    1730                1735                1740

Thr Gln Pro Leu Tyr Arg Gly Glu Leu Asn Glu His Leu Gly Leu
    1745                1750                1755

Leu Gly Pro Tyr Ile Arg Ala Glu Val Glu Asp Asn Ile Met Val
    1760                1765                1770

Thr Phe Arg Asn Gln Ala Ser Arg Pro Tyr Ser Phe Tyr Ser Ser
    1775                1780                1785

Leu Ile Ser Tyr Glu Glu Asp Gln Arg Gln Gly Ala Glu Pro Arg
    1790                1795                1800

Lys Asn Phe Val Lys Pro Asn Glu Thr Lys Thr Tyr Phe Trp Lys
    1805                1810                1815

Val Gln His His Met Ala Pro Thr Lys Asp Glu Phe Asx Asp Cys
    1820                1825                1830

Lys Ala Trp Ala Tyr Phe Ser Asp Val Asp Leu Glu Lys Asp Val
    1835                1840                1845

His Ser Gly Leu Ile Gly Pro Leu Leu Val Cys His Thr Asn Thr
    1850                1855                1860

Leu Asn Pro Ala His Gly Arg Gln Val Thr Val Gln Glu Phe Ala
    1865                1870                1875

Leu Phe Phe Thr Ile Phe Asp Glu Thr Lys Ser Trp Tyr Phe Thr
    1880                1885                1890

Glu Asn Met Glu Arg Asn Cys Arg Ala Pro Cys Asn Ile Gln Met
    1895                1900                1905

Glu Asp Pro Thr Phe Lys Glu Asn Tyr Arg Phe His Ala Ile Asn
    1910                1915                1920

Gly Tyr Ile Met Asp Thr Leu Pro Gly Leu Val Met Ala Gln Asp
    1925                1930                1935

Gln Arg Ile Arg Trp Tyr Leu Leu Ser Met Gly Ser Asn Glu Asn
    1940                1945                1950

Ile His Ser Ile His Phe Ser Gly His Val Phe Thr Val Arg Lys
    1955                1960                1965

Lys Glu Glu Tyr Lys Met Ala Leu Tyr Asn Leu Tyr Pro Gly Val
    1970                1975                1980

Phe Glu Thr Val Glu Met Leu Pro Ser Lys Ala Gly Ile Trp Arg
    1985                1990                1995

Val Glu Cys Leu Ile Gly Glu His Leu His Ala Gly Met Ser Thr
    2000                2005                2010

Leu Phe Leu Val Tyr Ser Asn Lys Cys Gln Thr Pro Leu Gly Met
    2015                2020                2025

Ala Ser Gly His Ile Arg Asp Phe Gln Ile Thr Ala Ser Gly Gln
    2030                2035                2040

Tyr Gly Gln Trp Ala Pro Lys Leu Ala Arg Leu His Tyr Ser Gly
    2045                2050                2055

Ser Ile Asn Ala Trp Ser Thr Lys Glu Pro Phe Ser Trp Ile Lys
    2060                2065                2070

Val Asp Leu Leu Ala Pro Met Ile Ile His Gly Ile Lys Thr Gln
    2075                2080                2085

Gly Ala Arg Gln Lys Phe Ser Ser Leu Tyr Ile Ser Gln Phe Ile
    2090                2095                2100
```

```
Ile Met Tyr Ser Leu Asp Gly Lys Lys Trp Gln Thr Tyr Arg Gly
    2105                2110                2115

Asn Ser Thr Gly Thr Leu Met Val Phe Phe Gly Asn Val Asp Ser
    2120                2125                2130

Ser Gly Ile Lys His Asn Ile Phe Asn Pro Pro Ile Ile Ala Arg
    2135                2140                2145

Tyr Ile Arg Leu His Pro Thr His Tyr Ser Ile Arg Ser Thr Leu
    2150                2155                2160

Arg Met Glu Leu Met Gly Cys Asp Leu Asn Ser Cys Ser Met Pro
    2165                2170                2175

Leu Gly Met Glu Ser Lys Ala Ile Ser Asp Ala Gln Ile Thr Ala
    2180                2185                2190

Ser Ser Tyr Phe Thr Asn Met Phe Ala Thr Trp Ser Pro Ser Lys
    2195                2200                2205

Ala Arg Leu His Leu Gln Gly Arg Ser Asn Ala Trp Arg Pro Gln
    2210                2215                2220

Val Asn Asn Pro Lys Glu Trp Leu Gln Val Asp Phe Gln Lys Thr
    2225                2230                2235

Met Lys Val Thr Gly Val Thr Gln Gly Val Lys Ser Leu Leu
    2240                2245                2250

Thr Ser Met Tyr Val Lys Glu Phe Leu Ile Ser Ser Ser Gln Asp
    2255                2260                2265

Gly His Gln Trp Thr Leu Phe Phe Gln Asn Gly Lys Val Lys Val
    2270                2275                2280

Phe Gln Gly Asn Gln Asp Ser Phe Thr Pro Val Val Asn Ser Leu
    2285                2290                2295

Asp Pro Pro Leu Leu Thr Arg Tyr Leu Arg Ile His Pro Gln Ser
    2300                2305                2310

Trp Val His Gln Ile Ala Leu Arg Met Glu Val Leu Gly Cys Glu
    2315                2320                2325

Ala Gln Asp Leu Tyr
    2330

<210> SEQ ID NO 6
<211> LENGTH: 8
<212> TYPE: PRT
<213> ORGANISM: Artificial
<220> FEATURE:
<223> OTHER INFORMATION: Factor VIII consensus insert sequence
<220> FEATURE:
<221> NAME/KEY: MISC_FEATURE
<222> LOCATION: (1)..(2)
<223> OTHER INFORMATION: Xaa can be S or T
<220> FEATURE:
<221> NAME/KEY: MISC_FEATURE
<222> LOCATION: (7)..(7)
<223> OTHER INFORMATION: Xaa can be S or T

<400> SEQUENCE: 6

Xaa Xaa Tyr Val Asn Arg Xaa Leu
1               5

<210> SEQ ID NO 7
<211> LENGTH: 8
<212> TYPE: PRT
<213> ORGANISM: Artificial
<220> FEATURE:
<223> OTHER INFORMATION: Factor VIII insert sequence

<400> SEQUENCE: 7
```

Thr Thr Tyr Val Asn Arg Ser Leu
1               5

<210> SEQ ID NO 8
<211> LENGTH: 8
<212> TYPE: PRT
<213> ORGANISM: Artificial
<220> FEATURE:
<223> OTHER INFORMATION: Factor VIII insert sequence

<400> SEQUENCE: 8

Thr Thr Tyr Val Asn Arg Thr Leu
1               5

<210> SEQ ID NO 9
<211> LENGTH: 8
<212> TYPE: PRT
<213> ORGANISM: Artificial
<220> FEATURE:
<223> OTHER INFORMATION: Factor VIII insert sequence

<400> SEQUENCE: 9

Thr Ser Tyr Val Asn Arg Ser Leu
1               5

<210> SEQ ID NO 10
<211> LENGTH: 8
<212> TYPE: PRT
<213> ORGANISM: Artificial
<220> FEATURE:
<223> OTHER INFORMATION: Factor VIII insert sequence

<400> SEQUENCE: 10

Thr Ser Tyr Val Asn Arg Thr Leu
1               5

<210> SEQ ID NO 11
<211> LENGTH: 8
<212> TYPE: PRT
<213> ORGANISM: Artificial
<220> FEATURE:
<223> OTHER INFORMATION: Factor VIII insert sequence

<400> SEQUENCE: 11

Ser Thr Tyr Val Asn Arg Ser Leu
1               5

<210> SEQ ID NO 12
<211> LENGTH: 8
<212> TYPE: PRT
<213> ORGANISM: Artificial
<220> FEATURE:
<223> OTHER INFORMATION: Factor VIII insert sequence

<400> SEQUENCE: 12

Ser Thr Tyr Val Asn Arg Thr Leu
1               5

<210> SEQ ID NO 13
<211> LENGTH: 8
<212> TYPE: PRT
<213> ORGANISM: Artificial
<220> FEATURE:
<223> OTHER INFORMATION: Factor VIII insert sequence

<400> SEQUENCE: 13

```
Ser Ser Tyr Val Asn Arg Ser Leu
1               5

<210> SEQ ID NO 14
<211> LENGTH: 8
<212> TYPE: PRT
<213> ORGANISM: Artificial
<220> FEATURE:
<223> OTHER INFORMATION: Factor VIII insert sequence

<400> SEQUENCE: 14

Ser Ser Tyr Val Asn Arg Thr Leu
1               5

<210> SEQ ID NO 15
<211> LENGTH: 5
<212> TYPE: PRT
<213> ORGANISM: Artificial
<220> FEATURE:
<223> OTHER INFORMATION: Factor VIII consensus insert sequence
<220> FEATURE:
<221> NAME/KEY: MISC_FEATURE
<222> LOCATION: (1)..(2)
<223> OTHER INFORMATION: Xaa can be S or T
<220> FEATURE:
<221> NAME/KEY: MISC_FEATURE
<222> LOCATION: (5)..(5)
<223> OTHER INFORMATION: Xaa can be S or T

<400> SEQUENCE: 15

Xaa Xaa Asn Asn Xaa
1               5

<210> SEQ ID NO 16
<211> LENGTH: 5
<212> TYPE: PRT
<213> ORGANISM: Artificial
<220> FEATURE:
<223> OTHER INFORMATION: Factor VIII insert sequence

<400> SEQUENCE: 16

Thr Thr Asn Asn Ser
1               5

<210> SEQ ID NO 17
<211> LENGTH: 5
<212> TYPE: PRT
<213> ORGANISM: Artificial
<220> FEATURE:
<223> OTHER INFORMATION: Factor VIII insert sequence

<400> SEQUENCE: 17

Thr Thr Asn Asn Thr
1               5

<210> SEQ ID NO 18
<211> LENGTH: 5
<212> TYPE: PRT
<213> ORGANISM: Artificial
<220> FEATURE:
<223> OTHER INFORMATION: Factor VIII insert sequence

<400> SEQUENCE: 18

Thr Ser Asn Asn Ser
1               5

<210> SEQ ID NO 19
<211> LENGTH: 5
```

```
<212> TYPE: PRT
<213> ORGANISM: Artificial
<220> FEATURE:
<223> OTHER INFORMATION: Factor VIII insert sequence

<400> SEQUENCE: 19

Thr Ser Asn Asn Thr
1               5

<210> SEQ ID NO 20
<211> LENGTH: 5
<212> TYPE: PRT
<213> ORGANISM: Artificial
<220> FEATURE:
<223> OTHER INFORMATION: Factor VIII insert sequence

<400> SEQUENCE: 20

Ser Thr Asn Asn Ser
1               5

<210> SEQ ID NO 21
<211> LENGTH: 5
<212> TYPE: PRT
<213> ORGANISM: Artificial
<220> FEATURE:
<223> OTHER INFORMATION: Factor VIII insert sequence

<400> SEQUENCE: 21

Ser Thr Asn Asn Thr
1               5

<210> SEQ ID NO 22
<211> LENGTH: 5
<212> TYPE: PRT
<213> ORGANISM: Artificial
<220> FEATURE:
<223> OTHER INFORMATION: Factor VIII insert sequence

<400> SEQUENCE: 22

Ser Ser Asn Asn Ser
1               5

<210> SEQ ID NO 23
<211> LENGTH: 5
<212> TYPE: PRT
<213> ORGANISM: Artificial
<220> FEATURE:
<223> OTHER INFORMATION: Factor VIII insert sequence

<400> SEQUENCE: 23

Ser Ser Asn Asn Thr
1               5

<210> SEQ ID NO 24
<211> LENGTH: 7
<212> TYPE: PRT
<213> ORGANISM: Artificial
<220> FEATURE:
<223> OTHER INFORMATION: O-linked glycosylation site consensus sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be S or T

<400> SEQUENCE: 24
```

```
Cys Xaa Xaa Gly Gly Xaa Cys
1               5

<210> SEQ ID NO 25
<211> LENGTH: 5
<212> TYPE: PRT
<213> ORGANISM: Artificial
<220> FEATURE:
<223> OTHER INFORMATION: O-linked glycosylation site sequence
<220> FEATURE:
<221> NAME/KEY: MISC_FEATURE
<222> LOCATION: (4)..(4)
<223> OTHER INFORMATION: Xaa can be D or E

<400> SEQUENCE: 25

Asn Ser Thr Xaa Ala
1               5

<210> SEQ ID NO 26
<211> LENGTH: 5
<212> TYPE: PRT
<213> ORGANISM: Artificial
<220> FEATURE:
<223> OTHER INFORMATION: O-linked glycosylation site sequence

<400> SEQUENCE: 26

Asn Ile Thr Gln Ser
1               5

<210> SEQ ID NO 27
<211> LENGTH: 5
<212> TYPE: PRT
<213> ORGANISM: Artificial
<220> FEATURE:
<223> OTHER INFORMATION: O-linked glycosylation site sequence

<400> SEQUENCE: 27

Gln Ser Thr Gln Ser
1               5

<210> SEQ ID NO 28
<211> LENGTH: 5
<212> TYPE: PRT
<213> ORGANISM: Artificial
<220> FEATURE:
<223> OTHER INFORMATION: O-linked glycosylation site sequence
<220> FEATURE:
<221> NAME/KEY: MISC_FEATURE
<222> LOCATION: (1)..(1)
<223> OTHER INFORMATION: Xaa can be D or E
<220> FEATURE:
<221> NAME/KEY: MISC_FEATURE
<222> LOCATION: (4)..(4)
<223> OTHER INFORMATION: Xaa can be R or K

<400> SEQUENCE: 28

Xaa Phe Thr Xaa Val
1               5

<210> SEQ ID NO 29
<211> LENGTH: 4
<212> TYPE: PRT
<213> ORGANISM: Artificial
<220> FEATURE:
<223> OTHER INFORMATION: O-linked glycosylation site sequence
<220> FEATURE:
<221> NAME/KEY: MISC_FEATURE
<222> LOCATION: (2)..(2)
<223> OTHER INFORMATION: Xaa can be D or E
```

```
<400> SEQUENCE: 29

Cys Xaa Ser Asn
1

<210> SEQ ID NO 30
<211> LENGTH: 5
<212> TYPE: PRT
<213> ORGANISM: Artificial
<220> FEATURE:
<223> OTHER INFORMATION: O-linked glycosylation site sequence
<220> FEATURE:
<221> NAME/KEY: MISC_FEATURE
<222> LOCATION: (5)..(5)
<223> OTHER INFORMATION: Xaa can be R or K

<400> SEQUENCE: 30

Gly Gly Ser Cys Xaa
1               5

<210> SEQ ID NO 31
<211> LENGTH: 30
<212> TYPE: PRT
<213> ORGANISM: Artificial
<220> FEATURE:
<223> OTHER INFORMATION: B domain deleted Factor VIII sequence

<400> SEQUENCE: 31

Leu Ser Lys Asn Asn Ala Ile Glu Pro Arg Ser Phe Ser Gln Asn Pro
1               5                   10                  15

Pro Val Leu Lys Arg His Gln Arg Glu Ile Thr Arg Thr Thr
            20                  25                  30

<210> SEQ ID NO 32
<211> LENGTH: 30
<212> TYPE: PRT
<213> ORGANISM: Artificial
<220> FEATURE:
<223> OTHER INFORMATION: Mutated B domain deleted Factor VIII sequence

<400> SEQUENCE: 32

Leu Ser Lys Asn Asn Thr Thr Glu Pro Arg Ser Phe Ser Gln Asn Pro
1               5                   10                  15

Pro Val Leu Lys Arg His Gln Arg Glu Ile Thr Arg Thr Thr
            20                  25                  30

<210> SEQ ID NO 33
<211> LENGTH: 31
<212> TYPE: PRT
<213> ORGANISM: Artificial
<220> FEATURE:
<223> OTHER INFORMATION: Mutated B domain deleted Factor VIII sequence

<400> SEQUENCE: 33

Leu Ser Lys Asn Asn Thr Thr Tyr Val Asn Arg Ser Leu Ser Gln Asn
1               5                   10                  15

Pro Pro Val Leu Lys Arg His Gln Arg Glu Ile Thr Arg Thr Thr
            20                  25                  30

<210> SEQ ID NO 34
<211> LENGTH: 28
<212> TYPE: PRT
<213> ORGANISM: Artificial
<220> FEATURE:
<223> OTHER INFORMATION: Mutated B domain deleted Factor VIII sequence
```

```
<400> SEQUENCE: 34

Leu Ser Lys Asn Asn Thr Thr Asn Asn Thr Ser Gln Asn Pro Pro Val
1               5                   10                  15

Leu Lys Arg His Gln Arg Glu Ile Thr Arg Thr Thr
                20                  25
```

OPTIMIZED HUMAN CLOTTING FACTOR VIII GENE EXPRESSION CASSETTES AND THEIR USE

STATEMENT OF PRIORITY

This application claims the benefit of U.S. Provisional Application Ser. No. 62/112,901, filed Feb. 6, 2015, the entire contents of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 5470-734_ST25.txt, 40,961 bytes in size, generated on Feb. 3, 2016 and filed via EFS-Web, is provided in lieu of a paper copy. This Sequence Listing is hereby incorporated by reference into the specification for its disclosures.

FIELD OF THE INVENTION

The invention relates to synthetic liver-specific promoters and expression constructs for producing polypeptides and functional nucleic acids in the liver of a subject. The invention further relates to Factor VIII proteins containing modifications in the amino acid sequence of the Factor VIII protein, as well as nucleic acid constructs encoding the Factor VIII proteins and methods of using these compositions to treat a bleeding disorder.

BACKGROUND OF THE INVENTION

Factor VIII (FVIII) plays a critical role in the coagulation cascade by accelerating the conversion of factor X to factor Xa. Deficiency in FVIII activity is responsible for the bleeding disorder hemophilia A. The current treatment for hemophilia A is intravenous infusion of plasma-derived or recombinant FVIII protein. Despite this treatment being effective in controlling bleeding episodes, the requirement for frequent infusion, owing to the short half-life of FVIII (8-12 hours), makes it inherently costly. Gene therapy has emerged as an attractive strategy for the eventual cure of this disease. However, the progress in delivering FVIII gene using one of the most promising viral vectors, adeno-associated virus (AAV), has lagged behind the progress in delivering coagulation factor IX because of the large size of the FVIII coding sequence approaching the packaging capacity of AAV.

The present invention overcomes shortcomings in the art by providing a short synthetic liver-specific promoter and expression construct suitable for use in AAV vectors. The invention further provides FVIII proteins comprising additional glycosylation sites with amino acid sequence modifications and methods of their use in treating bleeding disorders.

SUMMARY OF THE INVENTION

The present invention is based in part on the development of a synthetic liver-specific promoter that is only about 200 basepairs in length. The promoter may be used for producing polypeptides and functional nucleic acids in a liver-specific manner, especially using AAV vectors, which have strict length limitations and benefit from the availability of a short but strong promoter.

The present invention is further based in part on the development of modified FVIII proteins comprising additional glycosylation sites in the heavy chain. The modified proteins provide long-term and high level activity relative to FVIII proteins without the modifications described herein.

In one aspect, the present invention relates to a polynucleotide comprising a synthetic liver specific promoter, wherein the promoter comprises the nucleotide sequence of SEQ ID NO: 1 or a sequence at least 90% identical thereto.

In another aspect, the present invention relates to a vector, a cell, and/or a transgenic animal comprising the polynucleotide of the invention.

In a further aspect, the present invention relates to a method of producing a polypeptide or a functional nucleic acid in the liver of a subject, comprising delivering to the subject the polynucleotide, vector, and/or transformed cell of the invention, thereby producing the polypeptide or functional nucleic acid in the liver of the subject.

In an additional aspect, the present invention relates to a method of treating hemophilia A in a subject, comprising delivering to the subject a therapeutically effective amount of the polynucleotide, vector, and/or transformed cell of the invention, thereby treating hemophilia A in the subject.

In another aspect, the present invention relates to a method of increasing the bioavailability of a Factor VIII polypeptide in a subject, comprising delivering to the subject an effective amount of the polynucleotide, vector, and/or transformed cell of the invention, thereby increasing the bioavailability of the Factor VIII polypeptide in the subject.

In a further aspect, the present invention relates to a modified human Factor VIII polypeptide in which amino acid residues in the heavy chain are modified to create one or more glycosylation sites.

In an additional aspect, the present invention relates to a polynucleotide encoding the modified human Factor VIII polypeptide of the invention and a vector, a cell, and/or a transgenic animal comprising the polynucleotide.

In another aspect, the present invention relates to a method of producing Factor VIII in the liver of a subject, comprising delivering to the subject the polynucleotide encoding the modified human Factor VIII polypeptide of the invention or the vector and/or the transformed cell comprising the polynucleotide, thereby producing Factor VIII in the liver of the subject.

In a further aspect, the present invention relates to a method of treating hemophilia A in a subject, comprising delivering to the subject a therapeutically effective amount of the modified human Factor VIII polypeptide, polynucleotide, vector, and/or transformed cell of the invention, thereby treating hemophilia A in the subject.

In an additional aspect, the present invention relates to a method of increasing the bioavailability of a Factor VIII polypeptide in a subject, comprising delivering to the subject an effective amount of the polynucleotide encoding the modified human Factor VIII polypeptide of the invention or the vector and/or the transformed cell comprising the polynucleotide, thereby increasing the bioavailability of Factor VIII polypeptide in the subject.

These and other aspects of the invention are set forth in more detail in the description of the invention below.

BRIEF DESCRIPTION OF THE DRAWINGS

FIG. 4 shows the AAV-Lxp3.3i-BDD-F8 construct and the sequence of Lxp3.3i promoter-intron (SEQ ID NO: 2). ITR stands for the 145 bp inverted terminal repeat of AAV.

FIG. 5 shows FVIII expression from two constructs containing the non-specific CMV promoter or the liver-specific LXP3.3 promoter in human liver cancer Huh7 cells and mouse Hepa1-6 cells.

DETAILED DESCRIPTION OF THE INVENTION

Figures 1, 2A:
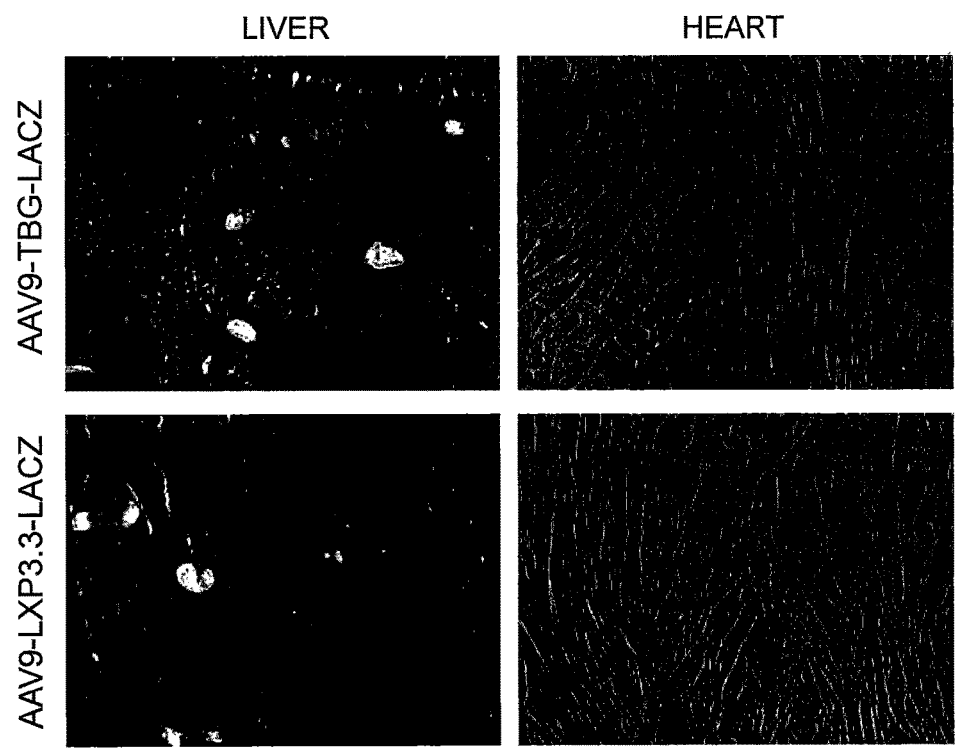
FIG. 1 shows the sequence of the LXP3.3 promoter (SEQ ID NO: 1). The putative hepatic and house-keeping transcriptional factor binding sites are highlighted by underlines.
FIG. 2A shows a comparison of LacZ expression in the liver and heart after intravenous injection of AAV9-TBG-LacZ or AAV9-Lxp3.3-LacZ into mice. Shown are X-gal and H&E double-staining of the liver and heart thin sections.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., New York).

Definitions

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity or other biological activity and the like, is meant to encompass variations of ±20%, ±10%, ±5%, ±1%, ±0.5%, or even ±0.1% of the specified amount.

The transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 USPQ 461, 463 (CCPA 1976) (emphasis in the original); see also MPEP § 2111.03.

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in coagulation-stimulating activity of at least about 50% or more as compared to the activity of a polypeptide consisting of the recited sequence.

The term "enhance" or "increase" or grammatical variations thereof as used herein refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectable activity (at most, an insignificant amount, e.g., less than about 10% or even 5%).

An "effective" amount as used herein is an amount that provides a desired effect.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

The efficacy of treating a bleeding disorder by the methods of the present invention can be determined by detecting a clinical improvement as indicated by a change in the subject's symptoms and/or clinical parameters as would be well known to one of skill in the art.

By the terms "treat," "treating," or "treatment," it is intended that the severity of the subject's condition is reduced or at least partially improved or modified and that some alleviation, mitigation or decrease in at least one clinical symptom is achieved.

The terms "prevent," "preventing," and "prevention" (and grammatical variations thereof) refer to a decrease or delay in the extent or severity of a disease, disorder and/or clinical symptom(s) after onset relative to what would occur in the absence of carrying out the methods of the invention prior to the onset of the disease, disorder and/or clinical symptom(s). In terms of hemophilia A, "preventing" refers to the occurrence of a lower number and/or severity of bleeding episodes than the number and/or severity of bleeding episodes that occur in the absence of the preventative treatment.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention.

An "isolated polynucleotide" is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence. An isolated polynucleotide that includes a gene is not a fragment of a chromosome that includes such gene, but rather includes the coding region and regulatory regions associated with the gene, but no additional genes naturally found on the chromosome.

The term "fragment," as applied to a polynucleotide, will be understood to mean a nucleotide sequence of reduced length relative to a reference nucleic acid or nucleotide sequence and comprising, consisting essentially of, and/or consisting of a nucleotide sequence of contiguous nucleotides identical or almost identical (e.g., 90%, 92%, 95%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of, and/or consist of oligonucleotides having a length of at least about 8, 10, 12, 15, 20, 25, 30, 35, 40, 45, 50, 75, 100, 150, 200, or more consecutive nucleotides of a nucleic acid or nucleotide sequence according to the invention.

The term "isolated" can refer to a nucleic acid, nucleotide sequence or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose.

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical or almost identical (e.g., 90%, 92%, 95%, 98%, 99% identical) to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral (e.g., plasmid) nucleic acid molecules for introducing a nucleic acid into a cell in vitro, ex vivo, and/or in vivo. A large number of vectors known in the art may be used to manipulate nucleic acids, incorporate response elements and promoters into genes, etc. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes), e.g., two, three, four, five or more heterologous nucleotide sequences.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, and adenovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

Vectors may be introduced into the desired cells by methods known in the art, e.g., transfection, electroporation, microinjection, transduction, cell fusion, DEAE dextran, calcium phosphate precipitation, lipofection (lysosome fusion), use of a gene gun, or a nucleic acid vector transporter (see, e.g., Wu et al., *J. Biol. Chem.* 267:963 (1992); Wu et al., *J. Biol. Chem.* 263:14621 (1988); and Hartmut et al., Canadian Patent Application No. 2,012,311, filed Mar. 15, 1990). In various embodiments, other molecules can be used for facilitating delivery of a nucleic acid in vivo, such as a cationic oligopeptide (e.g., WO95/21931), peptides derived from nucleic acid binding proteins (e.g., WO96/25508), and/or a cationic polymer (e.g., WO95/21931). It is also possible to introduce a vector in vivo as naked nucleic acid (see U.S. Pat. Nos. 5,693,622, 5,589,466 and 5,580,859). Receptor-mediated nucleic acid delivery approaches can also be used (Curiel et al., *Hum. Gene Ther.* 3:147 (1992); Wu et al., *J. Biol. Chem.* 262:4429 (1987)).

As used herein, the terms "protein" and "polypeptide" are used interchangeably and encompass both peptides and proteins, unless indicated otherwise.

A "fusion protein" is a polypeptide produced when two heterologous nucleotide sequences or fragments thereof coding for two (or more) different polypeptides not found fused together in nature are fused together in the correct translational reading frame. Illustrative fusion polypeptides include fusions of a polypeptide of the invention (or a fragment thereof) to all or a portion of glutathione-S-transferase, maltose-binding protein, or a reporter protein (e.g., Green Fluorescent Protein, β-glucuronidase, β-galactosidase, luciferase, etc.), hemagglutinin, c-myc, FLAG epitope, etc.

As used herein, a "functional" polypeptide or "functional fragment" is one that substantially retains at least one biological activity normally associated with that polypeptide (e.g., angiogenic activity, protein binding, ligand or receptor binding). In particular embodiments, the "functional" polypeptide or "functional fragment" substantially retains all of the activities possessed by the unmodified peptide. By "substantially retains" biological activity, it is meant that the polypeptide retains at least about 20%, 30%, 40%, 50%, 60%, 75%, 85%, 90%, 95%, 97%, 98%, 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even 5%). Biological activities such as protein binding and angiogenic activity can be measured using assays that are well known in the art and as described herein.

By the term "express" or "expression" of a polynucleotide coding sequence, it is meant that the sequence is transcribed, and optionally, translated. Typically, according to the present invention, expression of a coding sequence of the invention will result in production of the polypeptide of the invention. The entire expressed polypeptide or fragment can also function in intact cells without purification.

The term "adeno-associated virus" (AAV) in the context of the present invention includes without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, and ovine AAV and any other AAV now known or later discovered. See, e.g., BERNARD N. FIELDS et al., VIROLOGY, volume 2, chapter 69 (4th ed., Lippincott-Raven Publishers). A number of additional AAV serotypes and clades have been identified (see, e.g., Gao et al., (2004) *J. Virol.* 78:6381-6388 and Table 1), which are also encompassed by the term "AAV."

The genomic sequences of various AAV and autonomous parvoviruses, as well as the sequences of the ITRs, Rep proteins, and capsid subunits are known in the art. Such sequences may be found in the literature or in public databases such as the GenBank® database. See, e.g., GenBank® Accession Numbers NC 002077, NC 001401, NC 001729, NC 001863, NC 001829, NC 001862, NC 000883, NC 001701, NC 001510, AF063497, U89790, AF043303, AF028705, AF028704, J02275, J01901, J02275, X01457, AF288061, AH009962, AY028226, AY028223, NC 001358, NC 001540, AF513851, AF513852, AY530579, AY631965, AY631966; the disclosures of which are incorporated herein in their entirety. See also, e.g., Srivistava et al., (1983) *J. Virol.* 45:555; Chiorini et al., (1998) *J. Virol.* 71:6823; Chiorini et al., (1999) *J. Virol.* 73:1309; Bantel-Schaal et al., (1999) *J. Virol.* 73:939; Xiao et al., (1999) *J. Virol.* 73:3994; Muramatsu et al., (1996) *Virology* 221:208; Shade et al., (1986) *J. Virol.* 58:921; Gao et al., (2002) *Proc. Nat. Acad. Sci. USA* 99:11854; international patent publications WO 00/28061, WO 99/61601, WO 98/11244; U.S. Pat. No. 6,156,303; the disclosures of which are incorporated herein in their entirety. See also Table 1. An early description of the AAV1, AAV2 and AAV3 terminal repeat sequences is provided by Xiao, X., (1996), "Characterization of Adeno-associated virus (AAV) DNA replication and integration," Ph.D. Dissertation, University of Pittsburgh, Pittsburgh, Pa. (incorporated herein it its entirety).

A "recombinant AAV vector genome" or "rAAV genome" is an AAV genome (i.e., vDNA) that comprises at least one inverted terminal repeat (e.g., one, two or three inverted terminal repeats) and one or more heterologous nucleotide sequences. rAAV vectors generally retain the 145 base terminal repeat(s) (TR(s)) in cis to generate virus; however, modified AAV TRs and non-AAV TRs including partially or completely synthetic sequences can also serve this purpose. All other viral sequences are dispensable and may be supplied in trans (Muzyczka, (1992) *Curr. Topics Microbiol. Immunol.* 158:97). The rAAV vector optionally comprises two TRs (e.g., AAV TRs), which generally will be at the 5' and 3' ends of the heterologous nucleotide sequence(s), but need not be contiguous thereto. The TRs can be the same or different from each other. The vector genome can also contain a single ITR at its 3' or 5' end.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or the SV40 hairpin that serves as the origin of SV40 replication can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

An "AAV terminal repeat" or "AAV TR" may be from any AAV, including but not limited to serotypes 1, 2, 3, 4, 5, 6, 7, 8, 9, 10 or 11 or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

TABLE 1

| Complete Genomes | GenBank Accession Number |
| --- | --- |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu43 | AY530606 |
| Hu44 | AY530607 |
| Hu46 | AY530609 |
| Clade B | |
| Hu.19 | AY530584 |
| Hu.20 | AY530586 |
| Hu23 | AY530589 |
| Hu22 | AY530588 |
| Hu24 | AY530590 |
| Hu21 | AY530587 |
| Hu27 | AY530592 |
| Hu28 | AY530593 |
| Hu29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| HuT41 | AY695378 |
| HuS17 | AY695376 |
| HuT88 | AY695375 |
| HuT71 | AY695374 |
| HuT70 | AY695373 |
| HuT40 | AY695372 |
| HuT32 | AY695371 |
| HuT17 | AY695370 |
| HuLG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |

TABLE 1-continued

| Complete Genomes | GenBank Accession Number |
|---|---|
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV3 | NC_001729 |
| AAV3B | NC_001863 |
| AAV4 | NC_001829 |
| Rh34 | AY243001 |
| Rh33 | AY243002 |
| Rh32 | AY243003 |

The terms "rAAV particle" and "rAAV virion" are used interchangeably here. A "rAAV particle" or "rAAV virion" comprises a rAAV vector genome packaged within an AAV capsid.

The AAV capsid structure is described in more detail in BERNARD N. FIELDS et al., VIROLOGY, volume 2, chapters 69 & 70 (4th ed., Lippincott-Raven Publishers).

The term "pharmacokinetic properties" has its usual and customary meaning and refers to the absorption, distribution, metabolism and excretion of the FVIII protein.

The usual and customary meaning of "bioavailability" is the fraction or amount of an administered dose of a biologically active drug that reaches the systemic circulation. In the context of embodiments of the present invention, the term "bioavailability" includes the usual and customary meaning but, in addition, is taken to have a broader meaning to include the extent to which the FVIII protein is bioactive. In the case of FVIII, for example, one measurement of "bioavailability" is the procoagulant activity of FVIII protein obtained in the circulation post-infusion.

"Posttranslational modification" has its usual and customary meaning and includes but is not limited to removal of leader sequence, γ-carboxylation of glutamic acid residues, β-hydroxylation of aspartic acid residues, N-linked glycosylation of asparagine residues, O-linked glycosylation of serine and/or threonine residues, sulfation of tyrosine residues, phosphorylation of serine residues and any combination thereof.

As used herein, "biological activity" is determined with reference to a standard derived, e.g., from human plasma. For FVIII, the standard can be MONOCLATE-P® (CSL Behring). The biological activity of the standard is taken to be 100%.

The term "Factor VIII protein" or "FVIII protein" as used herein includes wild type FVIII protein as well as naturally occurring or man-made proteins (e.g., B domain deleted proteins). A FVIII protein of this invention can further include mutated forms of FVIII as are known in the literature. A FVIII protein of this invention further includes any other naturally occurring human FVIII protein or manmade human FVIII protein now known or later identified, and derivatives and active fragments/active domains thereof, as are known in the art.

The amino acid sequence of FVIII from multiple mammalian species is available from sequence databases such as GenBank. Examples of FVIII sequences are found in the table below.

| Species | GenBank Accession No. |
|---|---|
| Homo sapiens | AAA52484.1 |
| Mus musculus | NP_032003.2 |
| Sus scrofa | AAB06705.1 |
| Bos Taurus | NP_001138980.1 |
| Canis lupus familiaris | NP_001003212.1 |
| Rattus norvegicus | ADU79112.1 |

A FVIII protein of this invention further includes the pharmacologically active form of FVIII, which is the molecule from which the signal peptide has been removed and the B domain has been cleaved by the action of proteases (or by engineering it out of the protein by removing it at the nucleic acid level), resulting in two non-contiguous polypeptide chains for FVIII (light chain and heavy chain) folded as the functional FVIII clotting factor. Several B domain deleted forms of human FVIII are known, including the frequently used SQ version in which the residues between S743 and Q1638 are deleted. Specifically, FVIII proteins having a modification to increase the degree of glycosylation are specifically included in the broad term.

The amino acid sequence of human FVIII protein is well-known in the art and can be found, for example in GenBank Accession No. AAA52484. The human FVIII protein is 2351 amino acids in length and is comprised of a signal peptide (residues 1-19), heavy chain (residues 20-759), B domain (residues 760-1332), and light chain (residues 1668-2351). The amino acid sequence without the signal peptide is disclosed below (SEQ ID NO: 5).

The term "half life" is a broad term which includes the usual and customary meaning as well as the usual and customary meaning found in the scientific literature for FVIII. Specifically included in this definition is a measurement of a parameter associated with FVIII which defines the time post-infusion for a decrease from an initial value measured at infusion to half the initial value. In some embodiments, the half life of FVIII can be measured in blood and/or blood components using an antibody to FVIII in a variety of immunoassays, as are well known in the art and as described herein. Alternatively, half life may be measured as a decrease in FVIII activity using functional assays including standard clotting assays, as are well known in the art and as described herein.

The term "recovery" as used herein includes the amount of FVIII, as measured by any acceptable method including but not limited to FVIII antigen levels or FVIII protease or clotting activity levels, detected in a recipient animal or human subject (e.g., in the circulation) at the earliest practical time of removing a biological sample (e.g., a blood or blood product sample) for the purpose of measuring the level of FVIII following its infusion, injection, delivery or administration otherwise. With current methodologies, the earliest biological sampling time for measuring FVIII recovery typically falls within the first 15 minutes post infusion, injection, or delivery/administration otherwise of the FVIII, but it is reasonable to expect quicker sampling times as scientific and/or clinical technologies improve. In essence, the recovery value for FVIII is meant here to represent the maximum fraction of infused, injected or otherwise delivered/administered FVIII that can be measured in the recipient (e.g., in the circulation) at the earliest possible time point following infusion, injection, or other delivery to a recipient animal or patient.

The term "glycosylation site" is a broad term that has its usual and customary meaning. In the context of the present application the term applies to both sites that potentially could accept a carbohydrate moiety, as well as sites within the protein, specifically FVIII, on which a carbohydrate moiety has actually been attached and includes any amino acid sequence that could act as an acceptor for oligosaccharide and/or carbohydrate.

As used herein, a "transformed" cell is a cell that has been transformed, transduced and/or transfected with a nucleic acid molecule encoding a FVIII protein of this invention, including but not limited to a FVIII protein vector constructed using recombinant DNA techniques.

As used herein, the term "bleeding disorder" reflects any defect, congenital, acquired, or induced, of cellular, physiological, or molecular origin that is manifested in bleedings. Examples are clotting factor deficiencies (e.g., hemophilia A and B or deficiency of coagulation Factors XI, VII, VIII, or IX), clotting factor inhibitors, defective platelet function, thrombocytopenia, von Willebrand's disease, or bleeding induced by surgery or trauma.

Excessive bleedings also occur in subjects with a normally functioning blood clotting cascade (no clotting factor deficiencies or inhibitors against any of the coagulation factors) and may be caused by a defective platelet function, thrombocytopenia or von Willebrand's disease. In such cases, the bleedings may be likened to those bleedings caused by hemophilia because the haemostatic system, as in hemophilia, lacks or has abnormal essential clotting "compounds" (such as platelets or von Willebrand factor protein), causing major bleedings. In subjects who experience extensive tissue damage in association with surgery or trauma, the normal haemostatic mechanism may be overwhelmed by the demand of immediate hemostasis and they may develop bleeding in spite of a normal haemostatic mechanism. Achieving satisfactory hemostasis also is a problem when bleedings occur in organs such as the brain, inner ear region and eyes, with limited possibility for surgical hemostasis. The same problem may arise in the process of taking biopsies from various organs (liver, lung, tumor tissue, gastrointestinal tract) as well as in laparoscopic surgery. Common for all these situations is the difficulty to provide hemostasis by surgical techniques (sutures, clips, etc.), which also is the case when bleeding is diffuse (hemorrhagic gastritis and profuse uterine bleeding). Acute and profuse bleedings may also occur in subjects on anticoagulant therapy in whom a defective hemostasis has been induced by the therapy given. Such subjects may need surgical interventions in case the anticoagulant effect has to be counteracted rapidly. Radical retropubic prostatectomy is a commonly performed procedure for subjects with localized prostate cancer. The operation is frequently complicated by significant and sometimes massive blood loss. The considerable blood loss during prostatectomy is mainly related to the complicated anatomical situation, with various densely vascularized sites that are not easily accessible for surgical hemostasis, and which may result in diffuse bleeding from a large area. Also, intracerebral hemorrhage is the least treatable form of stroke and is associated with high mortality and hematoma growth in the first few hours following intracerebral hemorrhage. Another situation that may cause problems in the case of unsatisfactory hemostasis is when subjects with a normal haemostatic mechanism are given anticoagulant therapy to prevent thromboembolic disease. Such therapy may include heparin, other forms of proteoglycans, warfarin or other forms of vitamin K-antagonists as well as aspirin and other platelet aggregation inhibitors.

In one embodiment of the invention, the bleeding is associated with hemophilia. In another embodiment, the bleeding is associated with hemophilia with acquired inhibitors. In another embodiment, the bleeding is associated with thrombocytopenia. In another embodiment, the bleeding is associated with von Willebrand's disease. In another embodiment, the bleeding is associated with severe tissue damage. In another embodiment, the bleeding is associated with severe trauma. In another embodiment, the bleeding is associated with surgery. In another embodiment, the bleeding is associated with laparoscopic surgery. In another embodiment, the bleeding is associated with hemorrhagic gastritis. In another embodiment, the bleeding is profuse uterine bleeding. In another embodiment, the bleeding is occurring in organs with a limited possibility for mechanical hemostasis. In another embodiment, the bleeding is occurring in the brain, inner ear region or eyes. In another embodiment, the bleeding is associated with the process of taking biopsies. In another embodiment, the bleeding is associated with anticoagulant therapy.

A "subject" of the invention includes any animal having or susceptible to a bleeding disorder or bleeding condition for which control of bleeding is needed and/or desired, which can be treated, ameliorated or prevented by administration of FVIII to the subject, (such as hemophilia A and acquired FVIII deficiency (e.g., due to autoantibodies directed against FVIII or hematological malignancy)). Such a subject is generally a mammalian subject (e.g., a laboratory animal such as a rat, mouse, guinea pig, rabbit, primates, etc.), a farm or commercial animal (e.g., a cow, horse, goat, donkey, sheep, etc.), or a domestic animal (e.g., cat, dog, ferret, etc.). In particular embodiments, the subject is a primate subject, a non-human primate subject (e.g., a chimpanzee, baboon, monkey, gorilla, etc.) or a human. Subjects of the invention can be a subject known or believed to be at risk of a bleeding disorder or bleeding condition for which control is needed and/or desired. Alternatively, a subject according to the invention can also include a subject not previously known or suspected to be at risk of a bleeding disorder or bleeding condition for which control is needed or desired. As a further option, the subject can be a laboratory animal and/or an animal model of disease.

Subjects include males and/or females of any age, including neonates, juvenile, mature and geriatric subjects. With respect to human subjects, in representative embodiments, the subject can be an infant (e.g., less than about 12 months, 10 months, 9 months, 8 months, 7 months, 6 months, or younger), a toddler (e.g., at least about 12, 18 or 24 months and/or less than about 36, 30 or 24 months), or a child (e.g., at least about 1, 2, 3, 4 or 5 years of age and/or less than about 14, 12, 10, 8, 7, 6, 5, or 4 years of age). In embodiments of the invention, the subject is a human subject that is from about 0 to 3, 4, 5, 6, 9, 12, 15, 18, 24, 30, 36, 48 or 60 months of age, from about 3 to 6, 9, 12, 15, 18, 24, 30, 36, 48 or 60 months of age, from about 6 to 9, 12, 15, 18, 24, 30, 36, 48 or 60 months of age, from about 9 to 12, 15, 18, 24, 30, 36, 48 or 60 months of age, from about 12 to 18, 24, 36, 48 or 60 months of age, from about 18 to 24, 30, 36, 48 or 60 months of age, or from about 24 to 30, 36, 48 or 60 months of age.

Promoters and Expression Cassettes

One aspect of the present invention relates to a polynucleotide comprising a synthetic liver specific promoter, wherein the promoter comprises, consists essentially of, or consists of the nucleotide sequence of SEQ ID NO: 1 or a sequence at least about 90% identical thereto. In some embodiments, the nucleotide sequence is at least about 90%, 91%, 92%, 93%, 94%, 95%, 96%, 97%, 98%, or 99% identical to the nucleotide sequence of SEQ ID NQ: 1. The promoter is a short (about 200 basepairs) and strong liver-specific promoter that is ideal for liver specific expression of a polynucleotide of interest and is especially suited for use in AAV vectors due to its short length and the limited capacity of AAV vectors. The promoter was designed to contain a conserved basal promoter element and transcription initiation site. The basal promoter is linked at its 5' end with a number of liver-specific transcriptional factor binding sites for liver-specific expression (FIG. 1). The promoter exhibits high activity as initially identified in vitro using a luciferase reporter gene and transfection experiments in human liver cancer cell line Huh7 and then confirmed in vivo in mice.

In some embodiments, the promoter is part of an expression cassette in which it is operably linked to an intron, e.g., on the 3' end of the promoter. This may be done to increase the expression level of a polynucleotide of interest linked to the promoter. Any suitable intron may be used, e.g., the chimeric, intron CIN (Promega). In some embodiments, the intron is from VH4. In some embodiments, the intron may further comprise short non-native exon junction sequences. In one embodiment, the promoter and the intron together comprise, consist essentially of, or consist of the nucleotide sequence of SEQ ID NO: 2 or a sequence at least 90% identical thereto, e.g., at least about 90%, 91%, 92%, 93%, 94%, 95%, 96%, 97%, 98%, or 99% identical to the nucleotide sequence of SEQ ID NO: 1.

The promoter may be operably linked to a polynucleotide of interest. In some embodiments, the polynucleotide of interest encodes a polypeptide or a functional nucleic acid. In certain embodiments, the polynucleotide of interest encodes a clotting factor, e.g., FVIII, e.g., a B domain-deleted FVIII. The B domain-deleted FVIII may be encoded by a polynucleotide comprising, consisting essentially of, or consisting of the nucleotide sequence of SEQ ID NO: 3 or a sequence at least 90% identical thereto, e.g., at least about 90%, 91%, 92%, 93%, 94%, 95%, 96%, 97%, 98%, or 99% identical to the nucleotide sequence of SEQ ID NO: 3. In one embodiment, the expression cassette comprising the promoter, intron, and polynucleotide of interest encoding a B domain-deleted FVIII comprises, consists essentially of, or consists of the nucleotide sequence of SEQ ID NO: 4 or a sequence at least 90% identical thereto, e.g., at least about 90%, 91%, 92%, 93%, 94%, 95%, 96%, 97%, 98%, or 99% identical to the nucleotide sequence of SEQ ID NO: 4.

Another aspect of the invention is a vector, e.g., an expression vector, comprising the polynucleotide of the invention. The vector may be any type of vector known in the art, including, without limitation, plasmid vectors and viral vectors. In some embodiments, the viral vector is a retroviral or lentiviral vector. In some embodiments, the viral vector is an AAV vector from any known AAV serotype including without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, and ovine AAV and any other AAV now known or later discovered. In some embodiments, the AAV vector is AAV8 or AAV9.

A further aspect of the invention relates to a cell comprising the polynucleotide and/or vector of the invention (e.g., an isolated cell, a transformed cell, a recombinant cell, etc.). Thus, various embodiments of the invention are directed to recombinant host cells containing the vector (e.g., expression cassette). Such a cell can be isolated and/or present in a transgenic animal. Transformation of cells is described further below.

Another aspect of the invention relates to a transgenic animal comprising the polynucleotide, vector, and/or transformed cell of the invention. Transgenic animals are described further below.

The polynucleotide, vector and/or cell of this invention can be included in a pharmaceutical composition. Some embodiments are directed to a kit which includes the polynucleotide, vector and/or cell of this invention and/or reagents and/or instructions for using the kit, e.g., to carry out the methods of this invention.

Modified Factor VIII Proteins

One aspect of the invention relates to a modified mammalian Factor VIII polypeptide (e.g., human FVIII polypeptide) in which amino acid residues in the heavy chain are modified to create one or more additional glycosylation sites. In certain embodiments, the one or more additional glycosylation sites are in the C-terminus of the heavy chain, e.g., the last 100 amino acid residues of the heavy chain, e.g., the last 50, 40, 30, 20, 10, 9, 8, 7, 6, or 5 residues. In some embodiments, the polypeptide is modified to create at least 2 glycosylation sites, e.g., 2, 3, 4, 5, 6, 7, 8, 9, 10, 11, 12, 13, 14, or 15 or more glycosylation sites. The modifications may include amino acid substitutions, additions, deletions, or any combination thereof. These modifications are introduced into the amino acid sequence of the FVIII protein to produce a FVIII protein with increased activity upon expression in vivo.

By "additional" glycosylation sites is meant that the number of glycosylation sites in the FVIII protein is greater than the number of glycosylation sites normally present in a non-modified (e.g., wild-type) FVIII protein (e.g., SEQ ID NO: 5).

The present invention is further directed to FVIII proteins containing one or more (e.g., 2, 3, 4, 5, 6, 7, 8, 9, 10, 11, 12, 13, 14, 15, etc.) additional sugar side chains. Such additional sugar side chains can be present at one or more of the glycosylation sites in the FVIII proteins of this invention. Alternatively, the additional sugar side chains can be present at sites on the FVIII protein as a result of chemical and/or enzymatic methods to introduce such sugar chains to the FVIII molecule, as are well known in the art. By "additional" or "new" sugar chains is meant that the number of sugar chains in the FVIII protein is greater than the number of sugar chains normally present in a "wild type" form of FVIII. In various embodiments, about 1 to about 50 additional sugar side chains (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) can be added.

The glycosylation site(s) may be N-linked glycosylation site(s), O-linked glycosylation site(s) and a combination of N-linked glycosylation site(s) and O-linked glycosylation site(s). In some embodiments, the added glycosylation site(s) include N-linked glycosylation site(s) and the consensus sequence is NXT/S, with the proviso that X is not proline. In other embodiments, the glycosylation site(s) comprise O-linked glycosylation site(s) comprising a consensus sequence selected from the group consisting of CXXGGT/S-C (SEQ ID NO: 24), NSTE/DA (SEQ ID NO: 25), NITQS (SEQ ID NO: 26), QSTQS (SEQ ID NO: 27), D/E-FT-R/K-V (SEQ ID NO: 28), C-E/D-SN (SEQ ID NO: 29), GGSC-K/R (SEQ ID NO: 30) and any combination thereof.

In some embodiments about one to about 15 glycosylation site(s) can be added to the amino acid sequence of the FVIII protein of this invention. In various embodiments, about 1 to about 50 glycosylation site(s) (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) can be added.

As used herein, a "glycosylation attachment site" or "glycosylation site" can mean a sugar attachment consensus sequence (i.e., a series of amino acids that act as a consensus sequence for attaching a sugar (mono-, oligo-, or polysaccharide) to an amino acid sequence or it can mean the actual amino acid residue to which the sugar moiety is covalently linked. The sugar moiety can be a monosaccharide (simple sugar molecule), an oligosaccharide, or a polysaccharide.

In particular embodiments, additional amino acids can be inserted between and/or substituted into any of the amino acid residues that make up the heavy chain. Furthermore, the same insert of this invention can be introduced multiple times at the same and/or at different locations in the amino acid sequence of the FVIII protein. Also, different inserts and/or the same inserts can be introduced one or more times at the same and/or at different locations between amino acid residues throughout the amino acid sequence of the FVIII protein.

Some proteins can support a large number of sugar side chains and the distance between N-linked glycosylation sites can be as few as three, four, five or six amino acids (see, e.g., Lundin et al., *FEBS Lett.* 581:5601 (2007); Apweiler et al., *Biochim. Biophys. Acta* 1473:4 (1991), the entire contents of which are incorporated by reference herein).

In some embodiments, amino acid residues 736 and 737 of the wild-type human sequence (SEQ ID NO: 5) are substituted with amino acid residues XX, wherein X is S or T. Thus, residues 736 and 737 may be SS, ST, TS, or TT.

In some embodiments, amino acid residues 736-742 of the wild-type human sequence (SEQ ID NO: 5) are substituted with amino acid residues XXYVNRXL (SEQ ID NO: 6), wherein X is S or T. Thus, residues 736-742 may be the following.

| Residues 736-742 | SEQ ID NO |
|---|---|
| TTYVNRSL | 7 |
| TTYVNRTL | 8 |
| TSYVNRSL | 9 |
| TSYVNRTL | 10 |
| STYVNRSL | 11 |
| STYVNRTL | 12 |
| SSYVNRSL | 13 |
| SSYVNRTL | 14 |

In some embodiments, amino acid residues 736-742 of the wild-type human sequence (SEQ ID NO: 5) are substituted with amino acid residues XXNNX (SEQ ID NO: 15), wherein X is S or T. Thus, residues 736-740 may be the following.

| Residues 736-742 | SEQ ID NO |
|---|---|
| TTNNS | 16 |
| TTNNT | 17 |
| TSNNS | 18 |
| TSNNT | 19 |
| STNNS | 20 |
| STNNT | 21 |
| SSNNS | 22 |
| SSNNT | 23 |

In some embodiments, the modified human Factor VIII polypeptide is one in which the B domain is deleted, e.g., the SQ deletion from S743 to Gln1638 (as numbered in SEQ ID NO: 5).

FVIII proteins of this invention having additional glycosylation sites may be produced by recombinant methods such as site-directed mutagenesis using PCR. Alternatively, the FVIII protein of this invention may be chemically synthesized to prepare a FVIII protein with one or more (e.g., 1, 2, 3, 4, 5, 6, 7, 8, 9, 10, 11, 12, 13, 14, 15, etc.) additional glycosylation sites.

It is within the scope of this invention and within the skill of one of skill in the art to modify any amino acid residue or residues in the mature FVIII amino acid sequence according to methods well known in the art and as taught herein and to test any resulting FVIII protein for activity, stability, recovery, half life, etc., according to well known methods and as described herein (see, e.g., Elliott et al., *J. Biol. Chem.* 279:16854 (2004), the entire contents of which are incorporated by reference herein).

Embodiments of the invention are directed to recombinant FVIII proteins (e.g., X0, X1, X2) in which glycosylation sites have been added to improve the activity and/or recovery and/or half-life and/or stability of FVIII. The FVIII proteins of this invention comprise modifications that allow for increased bioavailability of the FVIII protein to a subject to whom the FVIII protein of this invention has been administered. Increased bioavailability in some embodiments refers to the standard current thinking in hematology that the concentration of FVIII in plasma is the relevant concentration. In some embodiments of the present invention, increased bioavailability refers to the ability of the FVIII protein to stay in a subject's circulation for a longer period of time. Accordingly, in some embodiments of the present invention, the FVIII proteins described herein are modified to result in a FVIII protein that has increased activity after in vivo expression and in some embodiments, the present invention provides a method of increasing the hemostatic effectiveness of a FVIII protein in a subject, comprising administering to the subject an effective amount of the FVIII protein of this invention, the polynucleotide of this invention, the vector of this invention and/or the cell of this invention, wherein the FVIII protein that is administered to the subject in any of these embodiments is a FVIII protein of this invention that has increased activity.

The FVIII proteins according to the invention are produced and characterized by methods well known in the art and as described herein. These methods include determination of clotting time (partial thromboplastin time (PPT) assay) and administration of the FVIII protein to a test animal to determine recovery, half life, and bioavailability by an appropriate immunoassay and/or activity-assay, as are well known in the art.

An additional aspect of the invention provides an isolated polynucleotide encoding the FVIII protein of this invention and an expression cassette for producing the FVIII protein.

Another aspect of the invention is a vector, e.g., an expression vector, comprising the polynucleotide of the invention. The vector may be any type of vector known in the art, including, without limitation, plasmid vectors and viral vectors. In some embodiments, the viral vector is an AAV vector from any known AAV serotype including without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, and ovine AAV and any other AAV now known or later discovered. In some embodiments, the AAV vector is AAV8 or AAV9.

A further aspect of the invention relates to a cell comprising the polynucleotide and/or vector of the invention (e.g., an isolated cell, a transformed cell, a recombinant cell, etc.). Thus, various embodiments of the invention are directed to recombinant host cells containing the vector (e.g., expression cassette). Such a cell can be isolated and/or present in a transgenic animal. Transformation of cells is described further below.

Another aspect of the invention relates to a transgenic animal comprising the polynucleotide, vector, and/or transformed cell of the invention. Transgenic animals are described further below.

The FVIII protein, polynucleotide, vector and/or cell of this invention can be included in a pharmaceutical composition. Some embodiments are directed to a kit which includes the FVIII protein, polynucleotide, vector and/or cell of this invention and/or reagents and/or instructions for using the kit, e.g., to carry out the methods of this invention.

Methods of the Invention

A further aspect of the invention relates to the use of the promoter and expression cassette of the invention to produce a polypeptide or a functional nucleic acid, e.g., in a liver specific manner. Thus, one aspect relates to a method of producing a polypeptide or a functional nucleic acid in the liver of a subject, comprising delivering to the subject the polynucleotide, vector, and/or transformed cell of the invention, thereby producing the polypeptide or functional nucleic acid in the liver of the subject. The polynucleotide, vector, and/or transformed cell are delivered under conditions whereby expression of the polynucleotide of interest occurs to produce a polypeptide or functional nucleic acid. Such conditions are well known in the art and described further below.

Another aspect of the invention relates to a method of treating hemophilia A or acquired factor VIII deficiency in a subject using the promoter and expression cassette of the invention, comprising delivering to the subject a therapeutically effective amount of the polynucleotide, vector, and/or transformed cell of the invention, thereby treating hemophilia A in the subject. In some embodiments, the polynucleotide of interest encodes a FVIII polypeptide as described above.

A further aspect of the invention relates to a method of increasing the bioavailability of a FVIII polypeptide in a subject using the promoter and expression cassette of the invention, comprising delivering to the subject an effective amount of the polynucleotide, vector, and/or transformed cell of the invention, thereby increasing the bioavailability of the FVIII polypeptide in the subject. In this aspect, the polynucleotide of interest encodes a FVIII polypeptide as described above.

The modified FVIII protein of this invention can be used in a method of treating a bleeding disorder by administering an effective amount of the FVIII protein to a subject (e.g., a human patient) in need thereof. Thus, the present invention also provides a method of treating a bleeding disorder comprising administering to a subject in need thereof an effective amount of the FVIII protein, the polynucleotide, the vector and/or the cell of this invention.

One aspect of the invention relates to a method of producing Factor VIII in the liver of a subject, comprising delivering to the subject the polynucleotide encoding the modified human Factor VIII polypeptide, vector, and/or transformed cell of the invention, thereby producing Factor VIII in the liver of the subject.

Another aspect of the invention relates to a method of treating hemophilia A or acquired factor VIII deficiency in a subject, comprising delivering to the subject a therapeutically effective amount of the modified human Factor VIII polypeptide, polynucleotide, vector, and/or transformed cell of the invention, thereby treating hemophilia A or acquired factor VIII deficiency in the subject.

A further aspect of the invention relates to a method of increasing the bioavailability of a Factor VIII polypeptide in a subject, comprising delivering to the subject an effective amount of the polynucleotide encoding the modified human Factor VIII polypeptide, vector, and/or transformed cell of the invention, thereby increasing the bioavailability of Factor VIII polypeptide in the subject.

Bleeding disorders that can be treated according to the methods of this invention include any disorder that can be treated with FVIII, such as hemophilia A and acquired FVIII deficiency. Such treatment protocols and dosing regimens for administering or delivering FVIII protein of this invention and/or a polynucleotide encoding a FVIII protein of this invention to a subject (e.g., a subject in need thereof) are well known in the art.

In embodiments of the invention, the dosage of a vector (e.g., a viral vector or other nucleic acid vector) encoding the FVIII protein of this invention can be in an amount such that a therapeutic plasma concentration of FVIII protein is achieved. A therapeutic concentration of FVIII protein is considered to be above 1% of the normal level of healthy individuals, which is measured on the average 100%, thus, one international unit (IU) of FVIII in 1 mL of normal human plasma. One of skill in the art would be able to determine the optimal dose for a given subject and a given condition.

For treatment in connection with deliberate interventions, the FVIII protein of the invention will typically be administered within about 24 hours prior to performing the intervention, and for as much as 7 days or more thereafter. Administration as a coagulant can be by a variety of routes as described herein.

The pharmaceutical compositions are primarily intended for parenteral administration for prophylactic and/or therapeutic treatment. Preferably, the pharmaceutical compositions are administered parenterally, i.e., intravenously, subcutaneously, or intramuscularly, or it may be administered by continuous or pulsatile infusion. Alternatively, the pharmaceutical compositions may be formulated for administration in various ways, including, but not limited to, orally, subcutaneously, intravenously, intracerebrally, intranasally, transdermally, intraperitoneally, intramuscularly, intrapulmonary, vaginally, rectally, intraocularly, or in any other acceptable manner.

The compositions for parenteral administration comprise the FVIII protein of the invention in combination with (e.g., dissolved in), a pharmaceutically acceptable carrier, preferably an aqueous carrier. A variety of aqueous carriers may be used, such as water, buffered water, 0.4% saline, 0.3% glycine and the like. The FVIII protein of the invention may also be formulated with compositions that prolong stability and storage, such as methionine and sucrose. The FVIII protein of the invention can also be formulated into liposome preparations for delivery or targeting to the site(s) of injury. Liposome preparations are generally described in, e.g., U.S. Pat. Nos. 4,837,028, 4,501,728, and 4,975,282. The compositions may be sterilized by conventional, well-known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. The compositions may also contain preservatives, isotonifiers, non-ionic surfactants or detergents, antioxidants and/or other miscellaneous additives.

The concentration of the FVIII protein in these formulations can vary widely, i.e., from less than about 0.5% by weight, usually at or at least about 1% by weight to as much as about 15 or 20% by weight and will be selected primarily by fluid volumes, viscosities, etc., in accordance with the particular mode of administration selected. Thus, as one nonlimiting example, a typical pharmaceutical composition for intravenous infusion could be made up to contain 250 ml of sterile Ringer's solution and 10 mg of the FVIII protein. Actual methods for preparing parenterally administrable compositions will be known or apparent to those skilled in the art and are described in more detail in, for example, *Remington's Pharmaceutical Sciences*, 21$^{st}$ ed., Mack Publishing Company, Easton, Pa. (2005).

The compositions comprising the FVIII protein of the present invention and/or nucleic acid molecules that encode the FVIII protein of the present invention can be administered for prophylactic and/or therapeutic treatments. In therapeutic applications, compositions are administered to a subject already suffering from a disease, as described above, in an amount sufficient to cure, alleviate or partially arrest the disease and its complications. An amount adequate to accomplish this is defined as a "therapeutically effective amount." As will be understood by the person skilled in the art amounts effective for this purpose will depend on the severity of the disease or injury as well as the weight and general state of the subject.

In prophylactic applications, compositions containing the FVIII polypeptide of the invention are administered to a subject susceptible to, or otherwise at risk of a disease state or injury to enhance the subject's own coagulative capability. Such an amount is defined to be a "prophylactically effective dose." In prophylactic applications, the precise amounts once again depend on the subject's state of health and weight.

Single or multiple administrations of the compositions can be carried out with dose levels and patterns being selected by the treating physician. For ambulatory subjects requiring daily maintenance levels, the FVIII protein may be administered by continuous infusion using e.g., a portable pump system.

The FVIII protein of the present invention may also be formulated in sustained, or extended release formulations. Methods of formulating sustained or extended release compositions are known in the art and include, but are not limited to, semi-permeable matrices of solid hydrophobic particles containing the polypeptide.

Local delivery of the FVIII protein of the present invention, such as, for example, topical application may be carried out, for example, by means of a spray, perfusion, double balloon catheters, stent, incorporated into vascular grafts or stents, hydrogels used to coat balloon catheters, or other well established methods. In any event, the pharmaceutical compositions should provide a quantity of FVIII protein sufficient to effectively treat the subject.

In some embodiments, the polynucleotide of interest (e.g., a FVIII protein) is delivered to the subject using an AAV vector. Thus, the invention also provides AAV virus particles (i.e., virions) comprising the polynucleotide of interest, wherein the virus particle packages (i.e., encapsidates) a vector genome, optionally an AAV vector genome.

In particular embodiments, the virion is a recombinant vector comprising a heterologous polynucleotide of interest, e.g., for delivery to a cell. Thus, the present invention is useful for the delivery of polynucleotides to cells in vitro, ex vivo, and in vivo. In representative embodiments, the recombinant vector of the invention can be advantageously employed to deliver or transfer polynucleotides to animal (e.g., mammalian) cells.

Any heterologous nucleotide sequence(s) may be delivered by a virus vector of the present invention. Polynucleotides of interest include polynucleotides encoding polypeptides, optionally therapeutic (e.g., for medical or veterinary uses) and/or immunogenic (e.g., for vaccines) polypeptides.

Therapeutic polypeptides include, but are not limited to, cystic fibrosis transmembrane regulator protein (CFTR), dystrophin (including the protein product of dystrophin mini-genes or micro-genes, see, e.g., Vincent et al., (1993) *Nature Genetics* 5:130; U.S. Patent Publication No. 2003017131; Wang et al., (2000) *Proc. Natl. Acad. Sci. USA* 97:13714-9 [mini-dystrophin]; Harper et al., (2002) *Nature Med.* 8:253-61 [micro-dystrophin]); mini-agrin, a laminin-α2, a sarcoglycan (α, β, γ or δ), Fukutin-related protein, myostatin pro-peptide, follistatin, dominant negative myostatin, an angiogenic factor (e.g., VEGF, angiopoietin-1 or 2), an anti-apoptotic factor (e.g., heme-oxygenase-1, TGF-β, inhibitors of pro-apoptotic signals such as caspases, proteases, kinases, death receptors [e.g., CD-095], modulators of cytochrome C release, inhibitors of mitochondrial pore opening and swelling); activin type II soluble receptor, anti-inflammatory polypeptides such as the Ikappa B dominant mutant, sarcospan, utrophin, mini-utrophin, antibodies or antibody fragments against myostatin or myostatin propeptide, cell cycle modulators, Rho kinase modulators such as Cethrin, which is a modified bacterial C3 exoenzyme [available from BioAxone Therapeutics, Inc., Saint-Lauren, Quebec, Canada], BCL-xL, BCL2, XIAP, FLICEc-s, dominant-negative caspase-8, dominant negative caspase-9, SPI-6 (see, e.g., U.S. Patent Application No. 20070026076), transcriptional factor PGC-α1, Pinch gene, ILK gene and thymosin β4 gene), clotting factors (e.g., Factor VIII, Factor IX, Factor X, etc.), erythropoietin, angiostatin, endostatin, catalase, tyrosine hydroxylase, an intracellular and/or extracellular superoxide dismutase, leptin, the LDL receptor, neprilysin, lipoprotein lipase, ornithine transcarbamylase, β-globin, α-globin, spectrin, $α_1$-antitrypsin, methyl cytosine binding protein 2, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, a cytokine (e.g., α-interferon, β-interferon, interferon-γ, interleukins-1 through -14, granulocyte-macrophage colony stimulating factor, lymphotoxin, and the like), peptide growth factors, neurotrophic factors and hormones (e.g., somatotropin, insulin, insulin-like growth factors including IGF-1 and IGF-2, GLP-1, platelet derived growth factor, epidermal growth factor, fibroblast growth factor, nerve growth factor, neurotrophic factor-3 and -4, brain-derived neurotrophic factor, glial derived growth factor, transforming growth factor-α and -β, and the like), bone morphogenic proteins (including RANKL and VEGF), a lysosomal protein, a glutamate receptor, a lymphokine, soluble CD4, an Fc receptor, a T cell receptor, ApoE, ApoC, inhibitor 1 of protein phosphatase inhibitor 1 (I-1), phospholamban, serca2a, lysosomal acid α-glucosidase, α-galactosidase A, Barkct, β2-adrenergic receptor, β2-adrenergic receptor kinase (BARK), phosphoinositide-3 kinase (PI3 kinase), calsarcin, a receptor (e.g., the tumor necrosis growth factor-α soluble receptor), an anti-inflammatory factor such as IRAP, Pim-1, PGC-1α, SOD-1, SOD-2, ECF-SOD, kallikrein, thymosin-β4, hypoxia-inducible transcription factor [HIF], an angiogenic factor, S100A1, parvalbumin, adenylyl cyclase type 6, a molecule that effects G-protein coupled receptor kinase type 2 knockdown such as a truncated constitutively active bARKct; phospholamban inhibitory or dominant-negative molecules such as phospholamban S16E, a monoclonal antibody (including single chain monoclonal antibodies) or a suicide gene product (e.g., thymidine kinase, cytosine deaminase, diphtheria toxin, and tumor necrosis factors such as TNF-α), and any other polypeptide that has a therapeutic effect in a subject in need thereof.

Heterologous nucleotide sequences encoding polypeptides include those encoding reporter polypeptides (e.g., an enzyme). Reporter polypeptides are known in the art and include, but are not limited to, a fluorescent protein (e.g., EGFP, GFP, RFP, BFP, YFP, or dsRED2), an enzyme that produces a detectable product, such as luciferase (e.g., from *Gaussia, Renilla,* or *Photinus*), β-galactosidase, β-glucuronidase, alkaline phosphatase, and chloramphenicol acetyltransferase gene, or proteins that can be directly detected. Virtually any protein can be directly detected by using, for example, specific antibodies to the protein. Additional markers (and associated antibiotics) that are suitable for either positive or negative selection of eukaryotic cells are disclosed in Sambrook and Russell (2001), *Molecular Cloning,* 3rd Ed., Cold Spring Harbor Laboratory Press, Cold Spring Harbor, N.Y., and Ausubel et al. (1992), *Current Protocols in Molecular Biology*, John Wiley & Sons, including periodic updates.

Alternatively, the heterologous nucleic acid may encode a functional RNA, e.g., an antisense oligonucleotide, a ribozyme (e.g., as described in U.S. Pat. No. 5,877,022), RNAs that effect spliceosome-mediated trans-splicing (see, Puttaraju et al., (1999) *Nature Biotech.* 17:246; U.S. Pat. Nos. 6,013,487; 6,083,702), interfering RNAs (RNAi) including small interfering RNAs (siRNA) that mediate gene silencing (see, Sharp et al., (2000) *Science* 287:2431), microRNA, or other non-translated "functional" RNAs, such as "guide" RNAs (Gorman et al., (1998) *Proc. Nat. Acad. Sci. USA* 95:4929; U.S. Pat. No. 5,869,248 to Yuan et al.), and the like. Exemplary untranslated RNAs include RNAi or antisense RNA against the multiple drug resistance (MDR) gene product (e.g., to treat tumors and/or for administration to the heart to prevent damage by chemotherapy), RNAi or antisense RNA against myostatin (Duchenne or Becker muscular dystrophy), RNAi or antisense RNA against VEGF or a tumor immunogen including but not limited to those tumor immunogens specifically described herein (to treat tumors), RNAi or antisense oligonucleotides targeting mutated dystrophins (Duchenne or Becker muscular dystrophy), RNAi or antisense RNA against the hepatitis B surface antigen gene (to prevent and/or treat hepatitis B infection), RNAi or antisense RNA against the HIV tat and/or rev genes (to prevent and/or treat HIV) and/or RNAi or antisense RNA against any other immunogen from a pathogen (to protect a subject from the pathogen) or a defective gene product (to prevent or treat disease). RNAi or antisense RNA against the targets described above or any other target can also be employed as a research reagent.

As is known in the art, anti-sense nucleic acids (e.g., DNA or RNA) and inhibitory RNA (e.g., microRNA and RNAi such as siRNA or shRNA) sequences can be used to induce "exon skipping" in patients with muscular dystrophy arising from defects in the dystrophin gene. Thus, the heterologous nucleic acid can encode an antisense nucleic acid or inhibitory RNA that induces appropriate exon skipping. Those skilled in the art will appreciate that the particular approach to exon skipping depends upon the nature of the underlying defect in the dystrophin gene, and numerous such strategies are known in the art. Exemplary antisense nucleic acids and inhibitory RNA sequences target the upstream branch point and/or downstream donor splice site and/or internal splicing enhancer sequence of one or more of the dystrophin exons (e.g., exons 19 or 23). For example, in particular embodiments, the heterologous nucleic acid encodes an antisense nucleic acid or inhibitory RNA directed against the upstream branch point and downstream splice donor site of exon 19 or 23 of the dystrophin gene. Such sequences can be incorporated into an AAV vector delivering a modified U7 snRNA and the antisense nucleic acid or inhibitory RNA (see, e.g., Goyenvalle et al., (2004) *Science* 306:1796-1799). As another strategy, a modified U1 snRNA can be incorporated into an AAV vector along with siRNA, microRNA or antisense RNA complementary to the upstream and downstream splice sites of a dystrophin exon (e.g., exon 19 or 23) (see, e.g., Denti et al., (2006) *Proc. Nat. Acad Sci. USA* 103:3758-3763). Further, antisense nucleic acids and inhibitory RNA can target the splicing enhancer sequences within exons 19, 43, 45 or 53 (see, e.g., U.S. Pat. Nos. 6,653,467; 6,727,355; and 6,653,466).

Ribozymes are RNA-protein complexes that cleave nucleic acids in a site-specific fashion. Ribozymes have specific catalytic domains that possess endonuclease activity (Kim et al., (1987) *Proc. Natl. Acad. Sci. USA* 84:8788; Gerlach et al., (1987) *Nature* 328:802; Forster and Symons, (1987) *Cell* 49:211). For example, a large number of ribozymes accelerate phosphoester transfer reactions with a high degree of specificity, often cleaving only one of several phosphoesters in an oligonucleotide substrate (Michel and Westhof, (1990) *J. Mol. Biol.* 216:585; Reinhold-Hurek and Shub, (1992) *Nature* 357:173). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, (1989) *Nature* 338:217). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of nucleic acid expression may be particularly suited to therapeutic applications (Scanlon et al., (1991) *Proc. Natl. Acad. Sci. USA* 88:10591; Sarver et al., (1990) *Science* 247:1222; Sioud et al., (1992) *J. Mol. Biol.* 223:831).

MicroRNAs (mir) are natural cellular RNA molecules that can regulate the expression of multiple genes by controlling the stability of the mRNA. Over-expression or diminution of a particular microRNA can be used to treat a dysfunction and has been shown to be effective in a number of disease states and animal models of disease (see, e.g., Couzin, (2008) *Science* 319:1782-4). The chimeric AAV can be used to deliver microRNA into cells, tissues and subjects for the treatment of genetic and acquired diseases, or to enhance functionality and promote growth of certain tissues. For example, mir-1, mir-133, mir-206 and/or mir-208 can be used to treat cardiac and skeletal muscle disease (see, e.g., Chen et al., (2006) *Genet.* 38:228-33; van Rooij et al., (2008) *Trends Genet.* 24:159-66). MicroRNA can also be used to modulate the immune system after gene delivery (Brown et al., (2007) *Blood* 110:4144-52).

The term "antisense oligonucleotide" (including "antisense RNA") as used herein, refers to a nucleic acid that is complementary to and specifically hybridizes to a specified DNA or RNA sequence. Antisense oligonucleotides and nucleic acids that encode the same can be made in accordance with conventional techniques. See, e.g., U.S. Pat. No. 5,023,243 to Tullis; U.S. Pat. No. 5,149,797 to Pederson et al.

Those skilled in the art will appreciate that it is not necessary that the antisense oligonucleotide be fully complementary to the target sequence as long as the degree of sequence similarity is sufficient for the antisense nucleotide sequence to specifically hybridize to its target (as defined above) and reduce production of the protein product (e.g., by at least about 30%, 40%, 50%, 60%, 70%, 80%, 90%, 95% or more).

To determine the specificity of hybridization, hybridization of such oligonucleotides to target sequences can be carried out under conditions of reduced stringency, medium stringency or even stringent conditions. Suitable conditions for achieving reduced, medium and stringent hybridization conditions are as described herein.

Alternatively stated, in particular embodiments, antisense oligonucleotides of the invention have at least about 60%, 70%, 80%, 90%, 95%, 97%, 98% or higher sequence identity with the complement of the target sequence and reduce production of the protein product (as defined above). In some embodiments, the antisense sequence contains 1, 2, 3, 4, 5, 6, 7, 8, 9 or 10 mismatches as compared with the target sequence.

Methods of determining percent identity of nucleic acid sequences are described in more detail elsewhere herein.

The length of the antisense oligonucleotide is not critical as long as it specifically hybridizes to the intended target and reduces production of the protein product (as defined above) and can be determined in accordance with routine procedures. In general, the antisense oligonucleotide is at least about eight, ten or twelve or fifteen nucleotides in length and/or less than about 20, 30, 40, 50, 60, 70, 80, 100 or 150 nucleotides in length.

RNA interference (RNAi) is another useful approach for reducing production of a protein product (e.g., shRNA or siRNA). RNAi is a mechanism of post-transcriptional gene silencing in which double-stranded RNA (dsRNA) corresponding to a target sequence of interest is introduced into a cell or an organism, resulting in degradation of the corresponding mRNA. The mechanism by which RNAi achieves gene silencing has been reviewed in Sharp et al., (2001) *Genes Dev* 15: 485-490; and Hammond et al., (2001) *Nature Rev. Gen.* 2:110-119). The RNAi effect persists for multiple cell divisions before gene expression is regained. RNAi is therefore a powerful method for making targeted knockouts or "knockdowns" at the RNA level. RNAi has proven successful in human cells, including human embryonic kidney and HeLa cells (see, e.g., Elbashir et al., *Nature* (2001) 411:494-8).

Initial attempts to use RNAi in mammalian cells resulted in antiviral defense mechanisms involving PKR in response to the dsRNA molecules (see, e.g., Gil et al., (2000) *Apoptosis* 5:107). It has since been demonstrated that short synthetic dsRNA of about 21 nucleotides, known as "short interfering RNAs" (siRNA) can mediate silencing in mammalian cells without triggering the antiviral response (see, e.g., Elbashir et al., *Nature* (2001) 411:494-8; Caplen et al., (2001) *Proc. Nat. Acad. Sci. USA* 98:9742).

The RNAi molecule (including an siRNA molecule) can be a short hairpin RNA (shRNA; see Paddison et al., (2002), *Proc. Nat. Acad. Sci. USA* 99:1443-1448), which is believed to be processed in the cell by the action of the RNase III like enzyme Dicer into 20-25mer siRNA molecules. The shRNAs generally have a stem-loop structure in which two inverted repeat sequences are separated by a short spacer sequence that loops out. There have been reports of shRNAs with loops ranging from 3 to 23 nucleotides in length. The loop sequence is generally not critical. Exemplary loop sequences include the following motifs: AUG, CCC, UUCG, CCACC, CTCGAG, AAGCUU, CCACACC and UUCAAGAGA.

The RNAi can further comprise a circular molecule comprising sense and antisense regions with two loop regions on either side to form a "dumbbell" shaped structure upon dsRNA formation between the sense and antisense regions. This molecule can be processed in vitro or in vivo to release the dsRNA portion, e.g., a siRNA.

International patent publication WO 01/77350 describes a vector for bi-directional transcription to generate both sense and antisense transcripts of a heterologous sequence in a eukaryotic cell. This technique can be employed to produce RNAi for use according to the invention.

Shinagawa et al., (2003) *Genes Dev.* 17:1340 reported a method of expressing long dsRNAs from a CMV promoter (a pol II promoter), which method is also applicable to tissue specific pol II promoters. Likewise, the approach of Xia et al., (2002) *Nature Biotech.* 20:1006, avoids poly(A) tailing and can be used in connection with tissue-specific promoters.

Methods of generating RNAi include chemical synthesis, in vitro transcription, digestion of long dsRNA by Dicer (in vitro or in vivo), expression in vivo from a delivery vector, and expression in vivo from a PCR-derived RNAi expression cassette (see, e.g., TechNotes 10(3) "Five Ways to Produce siRNAs," from Ambion, Inc., Austin Tex.; available at www.ambion.com).

Guidelines for designing siRNA molecules are available (see e.g., literature from Ambion, Inc., Austin Tex.; available at www.ambion.com). In particular embodiments, the siRNA sequence has about 30-50% G/C content. Further, long stretches of greater than four T or A residues are generally avoided if RNA polymerase III is used to transcribe the RNA. Online siRNA target finders are available, e.g., from Ambion, Inc. (www.ambion.com), through the Whitehead Institute of Biomedical Research (www.jura.wi.mit.edu) or from Dharmacon Research, Inc. (www.dharmacon.com).

The antisense region of the RNAi molecule can be completely complementary to the target sequence, but need not be as long as it specifically hybridizes to the target sequence (as defined above) and reduces production of the protein product (e.g., by at least about 30%, 40%, 50%, 60%, 70%, 80%, 90%, 95% or more). In some embodiments, hybridization of such oligonucleotides to target sequences can be carried out under conditions of reduced stringency, medium stringency or even stringent conditions, as defined above.

In other embodiments, the antisense region of the RNAi has at least about 60%, 70%, 80%, 90%, 95%, 97%, 98% or higher sequence identity with the complement of the target sequence and reduces production of the protein product (e.g., by at least about 30%, 40%, 50%, 60%, 70%, 80%, 90%, 95% or more). In some embodiments, the antisense region contains 1, 2, 3, 4, 5, 6, 7, 8, 9 or 10 mismatches as compared with the target sequence. Mismatches are generally tolerated better at the ends of the dsRNA than in the center portion.

In particular embodiments, the RNAi is formed by intermolecular complexing between two separate sense and antisense molecules. The RNAi comprises a ds region formed by the intermolecular basepairing between the two separate strands. In other embodiments, the RNAi comprises a ds region formed by intramolecular base pairing within a single nucleic acid molecule comprising both sense and antisense regions, typically as an inverted repeat (e.g., a shRNA or other stem loop structure, or a circular RNAi molecule). The RNAi can further comprise a spacer region between the sense and antisense regions.

Generally, RNAi molecules are highly selective. If desired, those skilled in the art can readily eliminate candidate RNAi that are likely to interfere with expression of nucleic acids other than the target by searching relevant databases to identify RNAi sequences that do not have substantial sequence homology with other known sequences, for example, using BLAST (available at www.ncbi.nlm.nih.gov/BLAST).

Kits for the production of RNAi are commercially available, e.g., from New England Biolabs, Inc. and Ambion, Inc.

The recombinant virus vector may also comprise a heterologous nucleotide sequence that shares homology with and recombines with a locus on the host chromosome. This approach may be utilized to correct a genetic defect in the host cell.

The present invention also provides recombinant virus vectors that express an immunogenic polypeptide, e.g., for vaccination. The heterologous nucleic acid may encode any immunogen of interest known in the art including, but are not limited to, immunogens from human immunodeficiency virus, influenza virus, gag proteins, tumor antigens, cancer antigens, bacterial antigens, viral antigens, and the like. Alternatively, the immunogen can be presented in the virus capsid (e.g., incorporated therein) or tethered to the virus capsid (e.g., by covalent modification).

The use of parvoviruses as vaccines is known in the art (see, e.g., Miyamura et al., (1994) *Proc. Nat. Acad. Sci. USA* 91:8507; U.S. Pat. No. 5,916,563 to Young et al., U.S. Pat. No. 5,905,040 to Mazzara et al., U.S. Pat. Nos. 5,882,652, 5,863,541 to Samulski et al.; the disclosures of which are incorporated herein in their entireties by reference). The antigen may be presented in the virus capsid. Alternatively, the antigen may be expressed from a heterologous nucleic acid introduced into a recombinant vector genome.

An immunogenic polypeptide, or immunogen, may be any polypeptide suitable for protecting the subject against a disease, including but not limited to microbial, bacterial, protozoal, parasitic, fungal and viral diseases. For example, the immunogen may be an orthomyxovirus immunogen (e.g., an influenza virus immunogen, such as the influenza virus hemagglutinin (HA) surface protein or the influenza virus nucleoprotein gene, or an equine influenza virus immunogen), or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogen may also be an arenavirus immunogen (e.g., Lassa fever virus immunogen, such as the Lassa fever virus nucleocapsid protein gene and the Lassa fever envelope glycoprotein gene), a poxvirus immunogen (e.g., vaccinia, such as the vaccinia L1 or L8 genes), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP genes), a bunyavirus immunogen (e.g., RVFV, CCHF, and SFS viruses), or a coronavirus immunogen (e.g., an infectious human coronavirus immunogen, such as the human coronavirus envelope glycoprotein gene, or a porcine transmissible gastroenteritis virus immunogen, or an avian infectious bronchitis virus immunogen, or a severe acute respiratory syndrome (SARS) immunogen such as a S [S1 or S2], M, E, or N protein or an immunogenic fragment thereof). The immunogen may further be a polio immunogen, herpes immunogen (e.g., CMV, EBV, HSV immunogens) mumps immunogen, measles immunogen, rubella immunogen, diphtheria toxin or other diphtheria immunogen, pertussis antigen, hepatitis (e.g., hepatitis A, hepatitis B or hepatitis C) immunogen, or any other vaccine immunogen known in the art.

Alternatively, the immunogen may be any tumor or cancer cell antigen. Optionally, the tumor or cancer antigen is expressed on the surface of the cancer cell. Exemplary cancer and tumor cell antigens are described in S. A.

Rosenberg, (1999) *Immunity* 10:281). Illustrative cancer and tumor antigens include, but are not limited to: BRCA1 gene product, BRCA2 gene product, gp100, tyrosinase, GAGE-1/2, BAGE, RAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J. Exp. Med.*, 180:347; Kawakami et al., (1994) *Cancer Res.* 54:3124) including MART-1 (Coulie et al., (1991) *J. Exp. Med.* 180:35), gp100 (Wick et al., (1988) *J. Cutan. Pathol.* 4:201) and MAGE antigen (MAGE-1, MAGE-2 and MAGE-3) (Van der Bruggen et al., (1991) *Science,* 254: 1643), CEA, TRP-1; TRP-2; P-15 and tyrosinase (Brichard et al., (1993) *J. Exp. Med.* 178:489); HER-2/neu gene product (U.S. Pat. No. 4,968,603); CA 125; HE4; LK26; FB5 (endosialin); TAG 72; AFP; CA19-9; NSE; DU-PAN-2; CA50; Span-1; CA72-4; HCG; STN (sialyl Tn antigen); c-erbB-2 proteins; PSA; L-CanAg; estrogen receptor; milk fat globulin; p53 tumor suppressor protein (Levine, (1993) *Ann. Rev. Biochem.* 62:623); mucin antigens (international patent publication WO 90/05142); telomerases; nuclear matrix proteins; prostatic acid phosphatase; papilloma virus antigens; and antigens associated with the following cancers: melanomas, adenocarcinoma, thymoma, sarcoma, lung cancer, liver cancer, colorectal cancer, non-Hodgkin's lymphoma, Hodgkin's lymphoma, leukemias, uterine cancer, breast cancer, prostate cancer, ovarian cancer, cervical cancer, bladder cancer, kidney cancer, pancreatic cancer, brain cancer, kidney cancer, stomach cancer, esophageal cancer, head and neck cancer and others (see, e.g., Rosenberg, (1996) *Annu. Rev. Med.* 47:481-91).

Alternatively, the heterologous nucleotide sequence may encode any polypeptide that is desirably produced in a cell in vitro, ex vivo, or in vivo. For example, the virus vectors may be introduced into cultured cells and the expressed protein product isolated therefrom.

It will be understood by those skilled in the art that the heterologous polynucleotide(s) of interest may be operably associated with appropriate control sequences. For example, the heterologous nucleic acid may be operably associated with expression control elements, such as transcription/translation control signals, origins of replication, polyadenylation signals, internal ribosome entry sites (IRES), promoters, enhancers, and the like.

Those skilled in the art will further appreciate that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence. By foreign, it is intended that the transcriptional initiation region is not found in the wild-type host into which the transcriptional initiation region is introduced.

Promoter/enhancer elements can be native to the target cell or subject to be treated and/or native to the heterologous nucleic acid sequence. The promoter/enhancer element is generally chosen so that it will function in the target cell(s) of interest. In representative embodiments, the promoter/enhancer element is a mammalian promoter/enhancer element. The promoter/enhance element may be constitutive or inducible.

Inducible expression control elements are generally used in those applications in which it is desirable to provide regulation over expression of the heterologous nucleic acid sequence(s). Inducible promoters/enhancer elements for gene delivery can be tissue-specific or tissue-preferred promoter/enhancer elements, and include muscle specific or preferred (including cardiac, skeletal and/or smooth muscle), neural tissue specific or preferred (including brain-specific), eye (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally employed for efficient translation of inserted protein coding sequences. These exogenous translational control sequences, which may include the ATG initiation codon and adjacent sequences, can be of a variety of origins, both natural and synthetic.

The present invention further provides methods of producing the virus vectors of the invention. In a representative embodiment, the present invention provides a method of producing a recombinant virus vector, the method comprising providing to a cell in vitro, (a) a template comprising (i) a polynucleotide of interest, and (ii) packaging signal sequences sufficient for the encapsidation of the AAV template into virus particles (e.g., one or more (e.g., two) terminal repeats, such as AAV terminal repeats), and (b) AAV sequences sufficient for replication and encapsidation of the template into viral particles (e.g., the AAV rep and AAV cap sequences). The template and AAV replication and capsid sequences are provided under conditions such that recombinant virus particles comprising the template packaged within the capsid are produced in the cell. The method can further comprise the step of collecting the virus particles from the cell. Virus particles may be collected from the medium and/or by lysing the cells.

In one illustrative embodiment, the invention provides a method of producing a rAAV particle comprising an AAV capsid, the method comprising: providing a cell in vitro with a nucleic acid encoding an AAV capsid, an AAV rep coding sequence, an AAV vector genome comprising a polynucleotide of interest, and helper functions for generating a productive AAV infection; and allowing assembly of the AAV particles comprising the AAV capsid and encapsidating the AAV vector genome.

The cell is typically a cell that is permissive for AAV viral replication. Any suitable cell known in the art may be employed, such as mammalian cells. Also suitable are trans-complementing packaging cell lines that provide functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an EBV based nuclear episome.

As a further alternative, the rep/cap sequences may be stably carried (episomal or integrated) within a cell.

Typically, the AAV rep/cap sequences will not be flanked by the AAV packaging sequences (e.g., AAV ITRs), to prevent rescue and/or packaging of these sequences.

The template (e.g., an rAAV vector genome) can be provided to the cell using any method known in the art. For example, the template may be supplied by a non-viral (e.g., plasmid) or viral vector. In particular embodiments, the template is supplied by a herpesvirus or adenovirus vector (e.g., inserted into the E1a or E3 regions of a deleted adenovirus). As another illustration, Palombo et al., (1998) *J. Virol.* 72:5025, describe a baculovirus vector carrying a reporter gene flanked by the AAV ITRs. EBV vectors may also be employed to deliver the template, as described above with respect to the rep/cap genes.

In another representative embodiment, the template is provided by a replicating rAAV virus. In still other embodiments, an AAV provirus is stably integrated into the chromosome of the cell.

To obtain maximal virus titers, helper virus functions (e.g., adenovirus or herpesvirus) essential for a productive AAV infection are generally provided to the cell. Helper virus sequences necessary for AAV replication are known in the art. Typically, these sequences are provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes required for efficient AAV production as described by Ferrari et al., (1997) *Nature Med.* 3:1295, and U.S. Pat. Nos. 6,040,183 and 6,093,570.

Further, the helper virus functions may be provided by a packaging cell with the helper genes integrated in the chromosome or maintained as a stable extrachromosomal element. In representative embodiments, the helper virus sequences cannot be packaged into AAV virions, e.g., are not flanked by AAV ITRs.

Those skilled in the art will appreciate that it may be advantageous to provide the AAV replication and capsid sequences and the helper virus sequences (e.g., adenovirus sequences) on a single helper construct. This helper construct may be a non-viral or viral construct, but is optionally a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector further contains the rAAV template. The AAV rep/cap sequences and/or the rAAV template may be inserted into a deleted region (e.g., the E1a or E3 regions) of the adenovirus.

In a further embodiment, the AAV rep/cap sequences and the adenovirus helper sequences are supplied by a single adenovirus helper vector. The rAAV template is provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as a "EBV based nuclear episome," see Margolski, (1992) *Curr. Top. Microbiol. Immun.* 158:67).

In a further exemplary embodiment, the AAV rep/cap sequences and adenovirus helper sequences are provided by a single adenovirus helper. The rAAV template is provided as a separate replicating viral vector. For example, the rAAV template may be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, in representative embodiments, the adenovirus helper sequences and the AAV rep/cap sequences are not flanked by the AAV packaging sequences (e.g., the AAV ITRs), so that these sequences are not packaged into the AAV virions.

Herpesvirus may also be used as a helper virus in AAV packaging methods. Hybrid herpesviruses encoding the AAV rep protein(s) may advantageously facilitate for more scalable AAV vector production schemes. A hybrid herpes simplex virus type I (HSV-1) vector expressing the AAV-2 rep and cap genes has been described (Conway et al., (1999) *Gene Therapy* 6:986 and WO 00/17377, the disclosures of which are incorporated herein in their entireties).

As a further alternative, the virus vectors of the invention can be produced in insect cells using baculovirus vectors to deliver the rep/cap genes and rAAV template as described by Urabe et al., (2002) *Human Gene Therapy* 13:1935-43.

Other methods of producing AAV use stably transformed packaging cells (see, e.g., U.S. Pat. No. 5,658,785).

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al., (1999) *Gene Therapy* 6:973). In representative embodiments, deleted replication-defective helper viruses are used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

The inventive packaging methods may be employed to produce high titer stocks of virus particles. In particular embodiments, the virus stock has a titer of at least about $10^5$ transducing units (tu)/ml, at least about $10^6$ tu/ml, at least about $10^7$ tu/ml, at least about $10^8$ tu/ml, at least about $10^9$ tu/ml, or at least about $10^{10}$ tu/ml.

In particular embodiments, the present invention provides a pharmaceutical composition comprising a virus vector of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a polynucleotide of interest to a cell in vitro. The virus vector may be introduced to the cells at the appropriate multiplicity of infection according to standard transduction methods appropriate for the particular target cells. Titers of the virus vector or capsid to administer can vary, depending upon the target cell type and number, and the particular virus vector or capsid, and can be determined by those of skill in the art without undue experimentation. In particular embodiments, at least about $10^3$ infectious units, more preferably at least about $10^5$ infectious units are introduced to the cell.

The cell(s) into which the virus vector can be introduced may be of any type, including but not limited to neural cells (including cells of the peripheral and central nervous systems, in particular, brain cells such as neurons, oligodendrocytes, glial cells, astrocytes), lung cells, cells of the eye (including retinal cells, retinal pigment epithelium, and corneal cells), epithelial cells (e.g., gut and respiratory epithelial cells), skeletal muscle cells (including myoblasts, myotubes and myofibers), diaphragm muscle cells, dendritic cells, pancreatic cells (including islet cells), hepatic cells, a cell of the gastrointestinal tract (including smooth muscle cells, epithelial cells), heart cells (including cardiomyocytes), bone cells (e.g., bone marrow stem cells), hematopoietic stem cells, spleen cells, keratinocytes, fibroblasts, endothelial cells, prostate cells, joint cells (including, e.g., cartilage, meniscus, synovium and bone marrow), germ cells, and the like. Alternatively, the cell may be any progenitor cell. As a further alternative, the cell can be a stem cell (e.g., neural stem cell, liver stem cell). As still a further alternative, the cell may be a cancer or tumor cell (cancers and tumors are described above). Moreover, the cells can be from any species of origin, as indicated above.

The virus vectors may be introduced to cells in vitro for the purpose of administering the modified cell to a subject. In particular embodiments, the cells have been removed from a subject, the virus vector is introduced therein, and the cells are then replaced back into the subject. Methods of removing cells from subject for treatment ex vivo, followed by introduction back into the subject are known in the art (see, e.g., U.S. Pat. No. 5,399,346). Alternatively, the recombinant virus vector is introduced into cells from another subject, into cultured cells, or into cells from any other suitable source, and the cells are administered to a subject in need thereof.

Suitable cells for ex vivo gene therapy are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ or about $10^3$ to about $10^6$ cells will be administered per dose in a pharmaceutically acceptable carrier. In particular embodiments, the cells transduced with the virus vector are administered to the subject in an effective amount in combination with a pharmaceutical carrier.

In some embodiments, cells that have been transduced with the virus vector may be administered to elicit an immunogenic response against the delivered polypeptide (e.g., expressed as a transgene or in the capsid). Typically, a quantity of cells expressing an effective amount of the polypeptide in combination with a pharmaceutically acceptable carrier is administered. Optionally, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the virus vectors of the invention to subjects. In particular embodiments, the method comprises a method of delivering a polynucleotide of interest to an animal subject, the method comprising: administering an effective amount of a virus vector according to the invention to an animal subject. Administration of the virus vectors of the present invention to a human subject or an animal in need thereof can be by any means known in the art. Optionally, the virus vector is delivered in an effective dose in a pharmaceutically acceptable carrier.

The virus vectors of the invention can further be administered to a subject to elicit an immunogenic response (e.g., as a vaccine). Typically, vaccines of the present invention comprise an effective amount of virus in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vectors to be administered to a subject will depend upon the mode of administration, the disease or condition to be treated, the individual subject's condition, the particular virus vector, and the nucleic acid to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^3$, $10^{14}$, $10^{15}$ transducing units or more, preferably about $10^7$ or $10^8$, $10^9$, $10^{10}$, $10^{11}$, $10^{12}$, $10^{13}$ or $10^{14}$ transducing units, yet more preferably about $10^{12}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, topical, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intro-lymphatic, and the like, as well as direct tissue or organ injection (e.g., to liver, skeletal muscle, cardiac muscle, diaphragm muscle or brain). Administration can also be to a tumor (e.g., in or a near a tumor or a lymph node). The most suitable route in any given case will depend on the nature and severity of the condition being treated and on the nature of the particular vector that is being used.

Delivery to any of these tissues can also be achieved by delivering a depot comprising the virus vector, which can be implanted into the tissue or the tissue can be contacted with a film or other matrix comprising the virus vector. Examples of such implantable matrices or substrates are described in U.S. Pat. No. 7,201,898).

The invention can be used to treat disorders of a tissue or organ. Alternatively, the invention can be practiced to deliver a nucleic acid to a tissue or organ, which is used as a platform for production of a protein product (e.g., an enzyme) or non-translated RNA (e.g., RNAi, microRNA, antisense RNA) that normally circulates in the blood or for systemic delivery to other tissues to treat a disorder (e.g., a metabolic disorder, such as diabetes (e.g., insulin), hemophilia (e.g., Factor IX or Factor VIII), or a lysosomal storage disorder (such as Gaucher's disease [glucocerebrosidase], Pompe disease [lysosomal acid α-glucosidase] or Fabry disease [α-galactosidase A]) or a glycogen storage disorder (such as Pompe disease [lysosomal acid α glucosidase]). Other suitable proteins for treating metabolic disorders are described above.

Injectables can be prepared in conventional forms, either as liquid solutions or suspensions, solid forms suitable for solution or suspension in liquid prior to injection, or as emulsions. Alternatively, one may administer the virus vector in a local rather than systemic manner, for example, in a depot or sustained-release formulation. Further, the virus vector can be delivered dried to a surgically implantable matrix such as a bone graft substitute, a suture, a stent, and the like (e.g., as described in U.S. Pat. No. 7,201,898).

Pharmaceutical compositions suitable for oral administration can be presented in discrete units, such as capsules, cachets, lozenges, or tablets, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a virus vector of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sublingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions suitable for parenteral administration can comprise sterile aqueous and non-aqueous injection solutions of the composition of this invention, which preparations are optionally isotonic with the blood of the intended recipient. These preparations can contain antioxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit/dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 µg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration can be presented as unit dose suppositories. These can be prepared by admixing the composition with one or more conventional solid carriers, such as for example, cocoa butter and then shaping the resulting mixture.

Pharmaceutical compositions of this invention suitable for topical application to the skin can take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, Pharm. Res. 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

The virus vectors disclosed herein may be administered to the lungs of a subject by any suitable means, for example, by administering an aerosol suspension of respirable particles comprised of the virus vectors, which the subject inhales. The respirable particles may be liquid or solid. Aerosols of liquid particles comprising the virus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors may likewise be produced with any solid particulate medicament aerosol generator, by techniques known in the pharmaceutical art.

Production of Factor VIII Proteins of this Invention

Many expression vectors can be used to create genetically engineered cells. Some expression vectors are designed to express large quantities of recombinant proteins after amplification of transfected cells under a variety of conditions that favor selected, high expressing cells. Some expression vectors are designed to express large quantities of recombinant proteins without the need for amplification under selection pressure. The present invention includes the production of genetically engineered cells according to methods standard in the art and is not dependent on the use of any specific expression vector or expression system.

To create a genetically engineered cell to produce large quantities of a FVIII protein, cells are transfected with an expression vector that contains a polynucleotide (e.g., cDNA) encoding the protein. In some embodiments, the FVIII protein is expressed with selected co-transfected enzymes that cause proper post-translational modification of the FVIII protein to occur in a given cell system.

The cell may be selected from a variety of sources, but is otherwise a cell that may be transfected with an expression vector containing a nucleic acid molecule (e.g., a cDNA) encoding a FVIII protein.

The practice of the present invention employs, unless otherwise indicated, conventional techniques of molecular biology, microbiology, recombinant DNA, and immunology, which are within the skill of the art. Such techniques are explained fully in the literature. See, e.g., Sambrook, et al., *Molecular Cloning; A Laboratory Manual,* 2nd ed. (1989); *DNA Cloning*, Vols. I and II (D. N Glover, ed. 1985); *Oligonucleotide Synthesis* (M. J. Gait, ed. 1984); *Nucleic Acid Hybridization* (B. D. Hames & S. J. Higgins, eds. 1984); *Transcription and Translation* (B. D. Hames & S. J. Higgins, eds. 1984); *Animal Cell Culture* (R. I. Freshney, ed. 1986); *Immobilized Cells and Enzymes* (IRL Press, 1986); B. Perbal, *A Practical Guide to Molecular Cloning* (1984); the series, *Methods in Enzymology* (Academic Press, Inc.), particularly Vols. 154 and 155 (Wu and Grossman, and Wu, eds., respectively); *Gene Transfer Vectors for Mammalian Cells* (J. H. Miller and M. P. Calos, eds. 1987, Cold Spring Harbor Laboratory); *Immunochemical Methods in Cell and Molecular Biology*, Mayer and Walker, eds. (Academic Press, London, 1987); Scopes, *Protein Purification: Principles and Practice,* 2nd ed. 1987 (Springer-Verlag, N.Y.); and *Handbook of Experimental Immunology* Vols I-IV (D. M. Weir and C. C. Blackwell, eds. 1986). All patents, patent applications, and publications cited in the specification are incorporated herein by reference in their entireties.

Genetic Engineering Techniques

The production of cloned genes, recombinant DNA, vectors, transformed cells, proteins and protein fragments by genetic engineering is well known. See, e.g., U.S. Pat. No. 4,761,371 to Bell et al. at Col. 6, line 3 to Col. 9, line 65; U.S. Pat. No. 4,877,729 to Clark et al. at Col. 4, line 38 to Col. 7, line 6; U.S. Pat. No. 4,912,038 to Schilling at Col. 3, line 26 to Col. 14, line 12; and U.S. Pat. No. 4,879,224 to Wallner at Col. 6, line 8 to Col. 8, line 59.

A vector is a replicable DNA construct. Vectors are used herein either to amplify nucleic acid encoding FVIII protein and/or to express nucleic acid which encodes FVIII protein. An expression vector is a replicable nucleic acid construct in which a nucleotide sequence encoding a FVIII protein is operably linked to suitable control sequences capable of effecting the expression of the nucleotide sequence to produce a FVIII protein in a suitable host cell. The need for such control sequences will vary depending upon the host cell selected and the transformation method chosen. Generally, control sequences include a transcriptional promoter, an optional operator sequence to control transcription, a sequence encoding suitable mRNA ribosomal binding sites, and sequences that control the termination of transcription and translation.

Vectors comprise plasmids, viruses (e.g., AAV, adenovirus, cytomegalovirus), phage, and integratable DNA fragments (i.e., fragments integratable into the host cell genome by recombination). The vector can replicates and function independently of the host cell genome (e.g., via transient expression), or can integrate into the host cell genome itself (e.g., stable integration). Expression vectors can contain a promoter and RNA binding sites that are operably linked to the nucleic acid molecule to be expressed and are operable in the host cell and/or organism.

DNA regions or nucleotide sequences are operably linked or operably associated when they are functionally related to each other. For example, a promoter is operably linked to a coding sequence if it controls the transcription of the sequence; or a ribosome binding site is operably linked to a coding sequence if it is positioned so as to permit translation of the sequence.

Suitable host cells include prokaryote, yeast or higher eukaryotic cells such as mammalian cells and insect cells. Cells derived from multicellular organisms are a particularly suitable host for recombinant FVIII protein synthesis, and mammalian cells are particularly preferred. Propagation of such cells in cell culture has become a routine procedure (*Tissue Culture*, Academic Press, Kruse and Patterson, editors (1973)). Examples of useful host cell lines are VERO and HeLa cells, Chinese hamster ovary (CHO) cell lines, and WI138, HEK 293, BHK, COS-7, CV, and MDCK cell lines. Expression vectors for such cells ordinarily include (if necessary) an origin of replication, a promoter located upstream from the nucleotide sequence encoding FVIII protein to be expressed and operatively associated therewith, along with a ribosome binding site, an RNA splice site (if intron-containing genomic DNA is used), a polyadenylation site, and a transcriptional termination sequence. In one embodiment, expression can be carried out in Chinese Hamster Ovary (CHO) cells using the expression system of U.S. Pat. No. 5,888,809, which is incorporated herein by reference in its entirety.

The transcriptional and translational control sequences in expression vectors to be used in transforming vertebrate cells are often provided by viral sources. Nonlimiting examples include promoters derived from polyoma, Adenovirus 2, and Simian Virus 40 (SV40). See, e.g., U.S. Pat. No. 4,599,308.

An origin of replication may be provided either by construction of the vector to include an exogenous origin, such as may be derived from SV 40 or other viral (e.g., polyoma, adenovirus, VSV, or BPV) source, or may be provided by the host cell chromosomal replication mechanism. If the vector is integrated into the host cell chromosome, the latter is often sufficient.

Rather than using vectors that contain a viral origin of replication, one can transform mammalian cells by the method of cotransformation with a selectable marker and the nucleic acid molecule encoding the FVIII protein. Nonlimiting examples of suitable selectable markers are dihydrofolate reductase (DHFR) or thymidine kinase. This method is further described in U.S. Pat. No. 4,399,216 which is incorporated by reference herein in its entirety.

Other methods suitable for adaptation to the synthesis of FVIII protein in recombinant vertebrate cell culture include those described in Gething et al. *Nature* 293:620 (1981); Mantei et al. *Nature* 281:40; and Levinson et al., EPO Application Nos. 117,060A and 117,058A, the entire contents of each of which are incorporated herein by reference.

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV, *Rachiplusia ou* MNPV, or *Galleria ou* MNPV) may be employed in carrying out the present invention, as described in U.S. Pat. Nos. 4,745,051 and 4,879,236 to Smith et al. In general, a baculovirus expression vector comprises a baculovirus genome containing the nucleotide sequence to be expressed inserted into the polyhedrin gene at a position ranging from the polyhedrin transcriptional start signal to the ATG start site and under the transcriptional control of a baculovirus polyhedrin promoter.

Prokaryote host cells include gram negative or gram positive organisms, for example *Escherichia coli* (*E. coli*) or bacilli, respectively. Higher eukaryotic cells include established cell lines of mammalian origin as described herein. Exemplary bacterial host cells are *E. coli* W3110 (ATCC 27,325), *E. coli* B, *E. coli* X1776 (ATCC 31,537) and *E. coli* 294 (ATCC 31,446). A broad variety of suitable prokaryotic and microbial vectors are available. *E. coli* is typically transformed using pBR322. Promoters most commonly used in recombinant microbial expression vectors include the betalactamase (penicillinase) and lactose promoter systems (Chang et at *Nature* 275:615 (1978); and Goeddel et al. *Nature* 281:544 (1979)), a tryptophan (trp) promoter system (Goeddel et al. *Nucleic Acids Res.* 8:4057 (1980) and EPO App. Publ. No. 36,776) and the tac promoter (De Boer et al. *Proc. Natl. Acad. Sci. USA* 80:21 (1983)). The promoter and Shine-Dalgarno sequence (for prokaryotic host expression) are operably linked to the nucleic acid encoding the FVIII protein, i.e., they are positioned so as to promote transcription of FVIII messenger RNA from DNA.

Eukaryotic microbes such as yeast cultures may also be transformed with protein-encoding vectors (see, e.g., U.S. Pat. No. 4,745,057). *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, nucleic acid encoding FVIII protein, sequences for polyadenylation and transcription termination, and a selection gene. An exemplary plasmid is YRp7, (Stinchcomb et al. *Nature* 282:39 (1979); Kingsman et al. *Gene* 7:141 (1979); Tschemper et al. *Gene* 10:157 (1980)). Suitable promoting sequences in yeast vectors include the promoters for metallothionein, 3-phosphoglycerate kinase (Hitzeman et al. *J. Biol. Chem.* 255:2073 (1980) or other glycolytic enzymes (Hess et al. *J. Adv. Enzyme Reg.* 7:149 (1968); and Holland et al. *Biochemistry* 17:4900 (1978)). Suitable vectors and promoters for use in yeast expression are further described in R. Hitzeman et al., EPO Publn. No. 73,657.

Cloned coding sequences of the present invention may encode FVIII of any species of origin, including mouse, rat, dog, opossum, rabbit, cat, pig, horse, sheep, cow, guinea pig, opossum, platypus, and human, but preferably encode FVIII protein of human origin. Nucleic acid encoding FVIII that is hybridizable with nucleic acid encoding proteins disclosed herein is also encompassed. Hybridization of such sequences may be carried out under conditions of reduced stringency or even stringent conditions (e.g., stringent conditions as represented by a wash stringency of 0.3M NaCl, 0.03M sodium citrate, 0.1% SDS at 60° C. or even 70° C.) to nucleic acid encoding FVIII protein disclosed herein in a standard in situ hybridization assay. See, e.g., Sambrook et al., *Molecular Cloning, A Laboratory Manual* (2d Ed. 1989) Cold Spring Harbor Laboratory).

The FVIII proteins produced according to the invention may be expressed in transgenic animals by known methods. See for example, U.S. Pat. No. 6,344,596, which is incorporated herein by reference in its entirety. In brief, transgenic animals may include but are not limited to farm animals (e.g., pigs, goats, sheep, cows, horses, rabbits and the like) rodents (such as mice, rats and guinea pigs), and domestic pets (for example, cats and dogs). Livestock animals such as pigs, sheep, goats and cows, are particularly preferred in some embodiments.

The transgenic animal of this invention is produced by introducing into a single cell embryo an appropriate polynucleotide that encodes a human FVIII protein of this invention in a manner such that the polynucleotide is stably integrated into the DNA of germ line cells of the mature animal, and is inherited in normal Mendelian fashion. The transgenic animal of this invention would have a phenotype of producing the FVIII protein in body fluids and/or tissues. The FVIII protein would be removed from these fluids and/or tissues and processed, for example for therapeutic use. (See, e.g., Clark et al. "Expression of human antihemophilic factor IX in the milk of transgenic sheep" *Bio/Technology* 7:487-492 (1989); Van Cott et al. "Haemophilic factors produced by transgenic livestock: abundance can enable alternative therapies worldwide" *Haemophilia* 10(4):70-77 (2004), the entire contents of which are incorporated by reference herein).

DNA molecules can be introduced into embryos by a variety of means including but not limited to microinjection, calcium phosphate mediated precipitation, liposome fusion, or retroviral infection of totipotent or pluripotent stem cells. The transformed cells can then be introduced into embryos and incorporated therein to form transgenic animals. Methods of making transgenic animals are described, for example, in *Transgenic Animal Generation and Use* by L. M. Houdebine, Harwood Academic Press, 1997. Transgenic animals also can be generated using methods of nuclear transfer or cloning using embryonic or adult cell lines as described for example in Campbell et al., *Nature* 380:64-66 (1996) and Wilmut et al., *Nature* 385:810-813 (1997). Further a technique utilizing cytoplasmic injection of DNA can be used as described in U.S. Pat. No. 5,523,222.

FVIII-producing transgenic animals can be obtained by introducing a chimeric construct comprising FVIII-encoding sequences. Methods for obtaining transgenic animals are well-known. See, for example, Hogan et al., *MANIPULATING THE MOUSE EMBRYO*, (Cold Spring Harbor Press 1986); Krimpenfort et al., *Bio/Technology* 9:88 (1991); Palmiter et al., *Cell* 41:343 (1985), Kraemer et al., *GENETIC MANIPULATION OF THE EARLY MAMMALIAN EMBRYO*, (Cold Spring Harbor Laboratory Press 1985); Hammer et al., *Nature* 315:680 (1985); Wagner et al., U.S. Pat. No. 5,175,385; Krimpenfort et al., U.S. Pat. No. 5,175,384, Janne et al., *Ann. Med.* 24:273 (1992), Brem et al., *Chim. Oggi.* 11:21 (1993), Clark et al., U.S. Pat. No. 5,476,995, all incorporated by reference herein in their entireties.

In some embodiments, cis-acting regulatory regions may be used that are "active" in mammary tissue in that the promoters are more active in mammary tissue than in other tissues under physiological conditions where milk is synthesized. Such promoters include but are not limited to the short and long whey acidic protein (WAP), short and long α, β and κ casein, α-lactalbumin and β-lactoglobulin ("BLG") promoters. Signal sequences can also be used in accordance with this invention that direct the secretion of expressed proteins into other body fluids, particularly blood and urine. Examples of such sequences include the signal peptides of secreted coagulation factors including signal peptides of FVIII, protein C, and tissue-type plasminogen activator.

Among the useful sequences that regulate transcription, in addition to the promoters discussed above, are enhancers, splice signals, transcription termination signals, polyadenylation sites, buffering sequences, RNA processing sequences and other sequences which regulate the expression of transgenes.

Preferably, the expression system or construct includes a 3' untranslated region downstream of the nucleotide sequence encoding the desired recombinant protein. This region can increase expression of the transgene. Among the 3' untranslated regions useful in this regard are sequences that provide a poly A signal.

Suitable heterologous 3'-untranslated sequences can be derived, for example, from the SV40 small t antigen, the casein 3' untranslated region, or other 3' untranslated sequences well known in this art. Ribosome binding sites are also important in increasing the efficiency of expression of FVIII. Likewise, sequences that regulate the post-translational modification of FVIII are useful in the invention.

Having described the present invention, the same will be explained in greater detail in the following examples, which are included herein for illustration purposes only, and which are not intended to be limiting to the invention.

Example 1

Synthetic Liver-Specific Promoter

We have designed and fully synthesized a number of artificial promoters that contain a conserved basal promoter element and transcription initiation site. The basal promoter is linked at its 5' end with a number of liver-specific transcriptional factor binding sites for liver-specific expression. A promoter named LXP3.3 (FIG. 1) (SEQ ID NO: 1) is selected due to its small size (200 bp) and high activity initially screened in vitro using a luciferase reporter gene and transfection experiments in human liver cancer cell line Huh7.

Figure 2B:
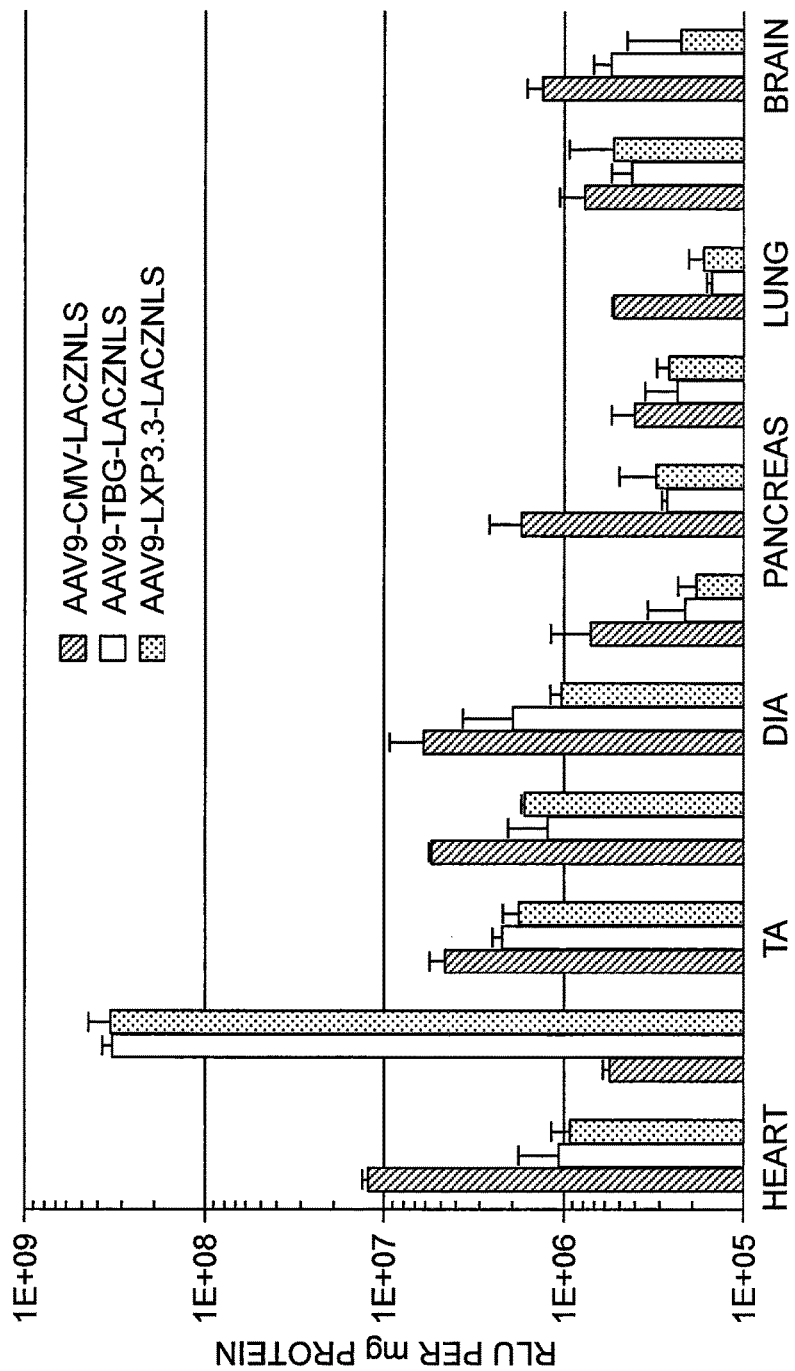
FIG. 2B shows a quantitative comparison of LacZ enzyme activities in various tissues of mice treated with $1\times10^{11}$ vector genomes (v.g.) of AAV9-LacZ vectors, which respectively contained the non-specific CMV promoter, the liver-specific TBG promoter or the LXP3.3 promoter (illustrated in FIG. 1).
Figure 2C:
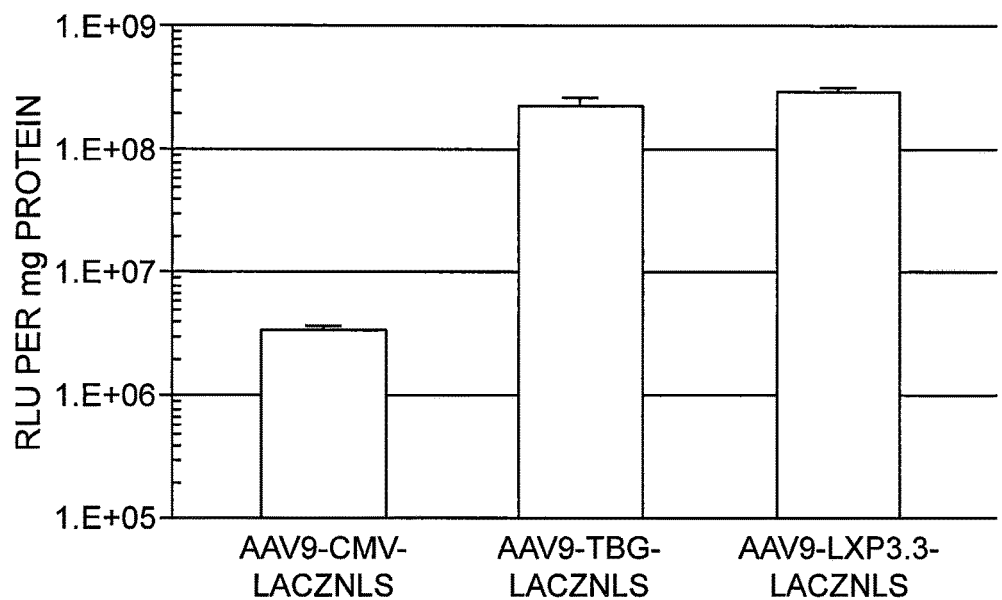
FIG. 2C shows a quantitative comparison of LacZ enzyme activities in the liver of mice treated with AAV9-LacZ vectors as shown in FIG. 2B but at a lower dose ($2\times10^{10}$ vector genomes (v.g.).

The LXP3.3 promoter was then further tested with a LacZ reporter gene packaged in an AAV9 vector that has a broad tissue tropism in the liver, heart and muscle, etc. Side by side in vivo experiments were done to compare the promoter activity and liver specificity with the strong and liver specific promoter thyroxine binding globulin (TBG), which was previously reported as one of the strongest liver-specific promoters in small and large animal models. The AAV9 vectors containing LXP3.3-LacZ or TBG-LacZ expression cassettes were injected into C56/B6 mice via the tail vein at two different doses. As shown in FIG. 2A, X-gal staining of the liver and the heart showed robust liver expression and lack of heart expression for both promoters. Quantitative analysis of tissue homogenates showed that these two promoters achieved nearly identical LacZ expression levels and tissue specificity toward the liver (FIG. 2B), although the LXP3.3 promoter was only 200 bp while the TBG was 681 bp in size. Specifically, quantitative LacZ enzyme activity analysis showed that the gene expression in the liver was more than 300 times higher than in the heart for the LXP3.3 and TBG promoters. In addition, the LacZ enzyme activities obtained by the liver-specific promoters were 500 times higher in the liver than the activities obtained by the ubiquitous CMV promoter (FIG. 2C). On the other hand, the CMV promoter achieved LacZ expression in the heart nearly 13 times as high as the liver-specific promoters did (FIG. 2B). The results demonstrated that the synthetic promoter LXP3.3 is highly active and specific in the liver.

Example 2

Synthetic Promoter Intron Cassette

Figure 3:
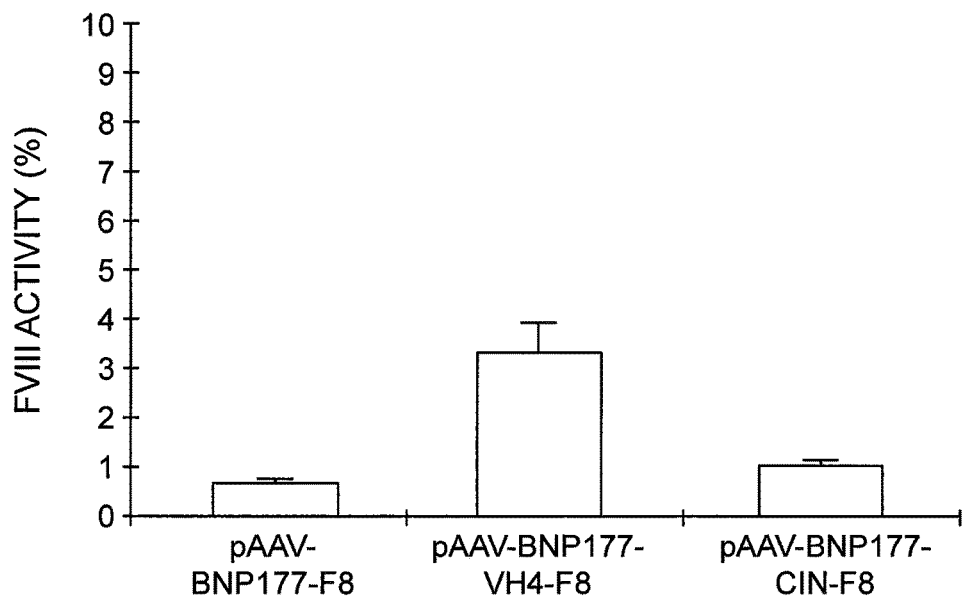
FIG. 3 shows Factor VIII activity in the supernatant of Huh7 cells transfected with different AAV vector plasmids, which contained a NBP promoter (177 bp) driving the human BDD factor VIII gene without an intron, or with a VH4 intron or a chimeric CIN intron.

The fully synthesized promoter LXP3.3 was linked at its 3' end to a small intron of VH4 with short non-native exon junction sequences. This intron was initially tested by in vitro transfection experiment using a weak promoter driving the BDD human FVIII gene. The addition of the VH4 intron rendered a much higher gene expression than the promoter without intron and also rendered higher expression than a commonly used chimeric intron CIN (Promega) (FIG. 3). As a result, we combined the LXP3.3 promoter and VH4 intron with artificial exon junction sequences and named it as LXP3.3I (SEQ ID NO: 2). To test its activity in driving FVIII expression, we inserted the promoter LXP3.3I upstream of a fully synthesized human BDD deleted FVIII gene (SEQ ID NO: 3), which is followed by a small poly adenylation site. The entire gene expression cassette (SEQ ID NO: 4) was subsequently cloned into AAV vector plasmid backbone that has two AAV inverted terminal repeat sequences for vector DNA replication and vector genome packaging (FIG. 4).

Figure 6:
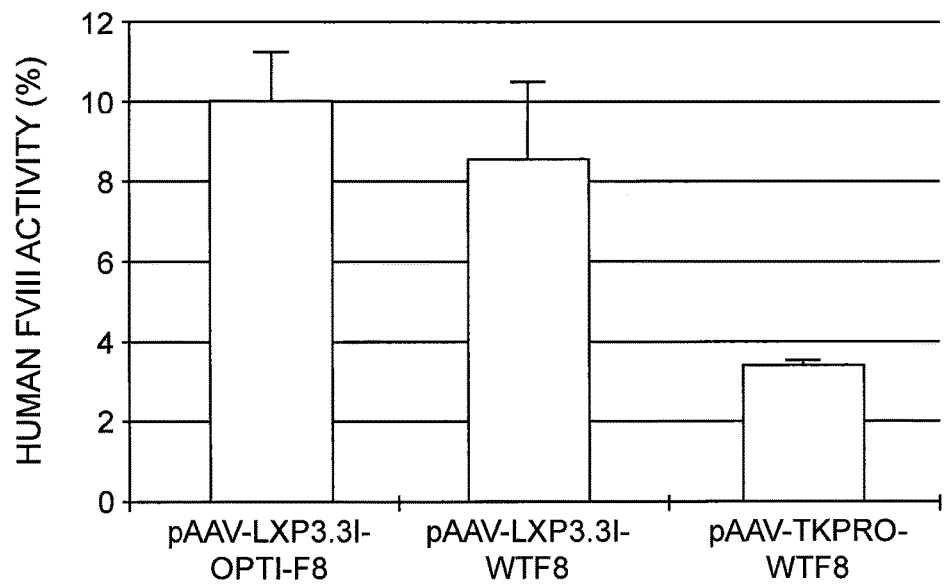
FIG. 6 shows FVIII activity in Huh7 cells respectively transfected with different BDD Factor VIII (synthesized opti-F8 or wild type wtF8) plasmids respectively contain promoter LXP3.3 or a weak promoter TkPro.

To compare the promoter activities in vitro, the ubiquitous CMV promoter linked to the SV40 intron, a commonly used strong combination, was used to replace the LXP3.3I in the FVIII expression cassette. After transfection of the plasmids into the human liver cancer cell line Huh7, FVIII activities were measured with a chromogenic kit. As shown in the transfection experiment in FIG. 5, the LXP3.3I gave rise to higher FVIII activities in the cell culture media than the CMV promoter did. In addition, we also compared the fully synthesized human BDD deleted FVIII gene with the BDD FVIII gene of native human DNA sequences in a transfection experiment. When driven by the same LXP3.3I, the two genes that encoded the same FVIII amino acids sequence but used different choice of codons showed no significant difference in FVIII activities in human cell (FIG. 6). However, when a different liver-specific promoter was used, the BDD FVIII gene with native codons showed lower expression when compared with the same gene driven by the LXP3.3I, suggesting that it was mainly due to the LXP3.3I promoter that resulted in higher gene expression.

Figure 7A:
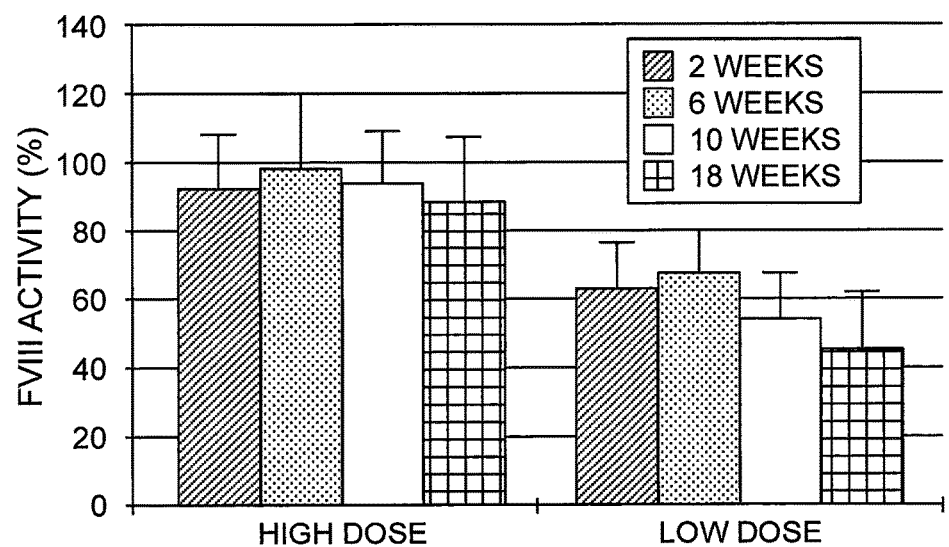
FIG. 7A shows AAV9-Lxp3.3-F8 mediated long-term human FVIII gene expression and FVIII activity in FVIII knockout mice, after IV injection of a high dose ($2\times10^{11}$ v.g./mouse) or a low dose ($4\times10^{10}$ v.g./mouse). Factor VIII activities (as percentage of normal human levels) were measure at 2, 6, 10 and 18 weeks post-injection respectively.
Figure 7B:
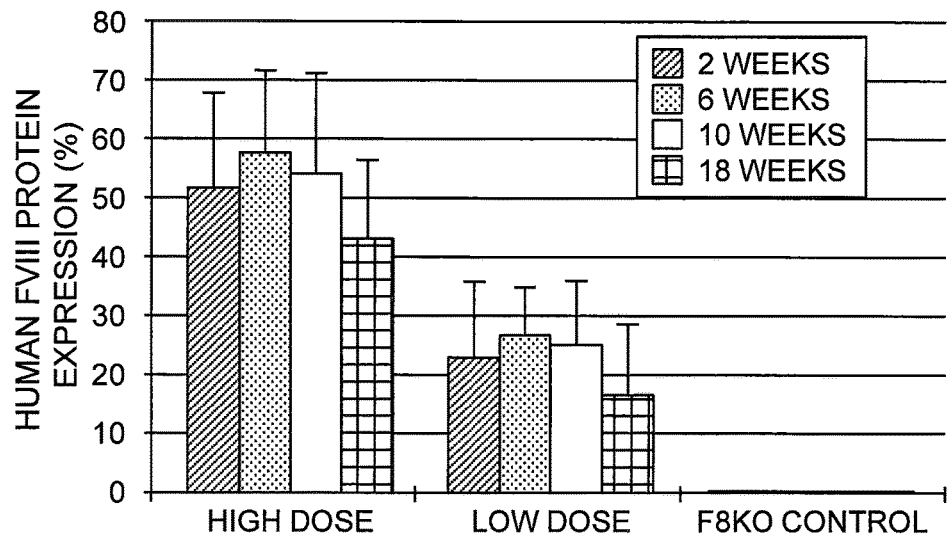
FIG. 7B shows AAV9-Lxp3.3-F8 mediated long-term human FVIII gene expression and human FVIII protein concentrations in FVIII knockout mice, after IV injection of a high dose ($2\times10^{11}$ v.g./mouse) or a low dose ($4\times10^{10}$ v.g./mouse). Factor VIII proteins were measure by ELISA (as percentage of normal human levels) at 2, 6, 10 and 18 weeks post-injection respectively.

We next tested the gene expression activities in vivo in a commonly used FVIII gene knockout hemophilia A mouse model. The LXP3.3I-hF8 gene expression cassette was packaged into AAV9 capsid and injected into the tail vein of the FVIII KO mice. Two different doses of vector were used ($2 \times 10^{11}$ and $4 \times 10^{10}$ vector genomes per mouse) to examine the in vivo expression. As shown in FIG. 7A, high level and long-term gene expression was achieved at these two doses for more than 1 year after vector administration. In addition to the chromogenic assay for FVIII activities, the ELISA assay was also used to examine the quantity of FVIII protein secreted in the plasma (FIG. 7B). The result showed that the BDD FVIII protein concentrations, compared to the reference standard of the full-length wild-type human FVIII protein, were approximately 50% lower than the readings that were obtained by the chromogenic assay for FVIII activities against the same full-length human FVIII. This discrepancy, the lower ELISA reading than the FVIII activity reading, is likely due to the lack of the long B-domain in the BDD FVIII, which comprises nearly half of the wild type FVIII in length. Since the ELISA kit used polyclonal antibodies against the wild-type full-length FVIII including the B-domain, it is expected that the BDD FVIII lacking the B-domain had fewer antibody binding sites and therefore a lower ELISA reading. These results indicated that both the chromogenic assay and the ELISA assay produced consistent measurement of the FVIII expression in the hemophilia A mice. A partial thromboplastin time (PTT) assay was also performed at a few time points. The results were in general agreement with those of the other two assays.

Example 3

Factor VIII Heavy Chain Mutations

Previous literature has shown that the heavy chain of the FVIII is the limiting factor. The heavy chain is much less effectively processed and/or much less stable than the light chain, of which the precise mechanisms remain obscure. For example, when the heavy chain and light chain genes were separately expressed from two separate vectors, much higher copy numbers of the heavy chain gene was required than the light chain gene, in order to obtain similar protein concentrations for clotting activities. As a result, we set out to enhance the FVIII heavy chain post translational processing efficiency by introducing mutations at its C-terminal region, specifically, by introducing new glycosylation sites, because glycosylation is well known for its role in post translational processing and stability of cell membrane-associated and secreted proteins. We chose to introduce the glycosylation at the C-terminus of the heavy chain. The rationale was that because this terminal region is amorphous as shown by the X-ray crystal structure analysis of the BDD FVIII protein, it is therefore a flexible region without defined structure. Hence, mutations in that region are likely not to disturb the FVIII protein functional structures. With that rationale, we took advantage of two native asparagine at positions 734 and 735, and mutated their adjacent amino acids 736 and 737 to threonines (NNAI to NNTT). The mutations minimize the alteration of amino acid sequences and maximize the degree of glycosylation, creating two de novo glycosylation sites (NNT and NTT) in mutant FVIII named X0 (FIG. 8).

In addition to the two new glycosylation sites in mutant X0, we have added another glycosylation site right next to the NNTT site by replacing the peptide (EPRSF) at amino acids 738-742 of the N-terminus in the heavy chain (with a native glycosylation sequence (YVNRSL), which was isolated from amino acids 237 to 242. This native glycosylation site (NRS) was chosen because it is one of the most effectively glycosylated sites in the heavy chain (Medzihradszky et al., *Anal. Chem.* 69:3986 (1997)), generating mutant FVIII named X1 (FIG. 8).

Figure 8:
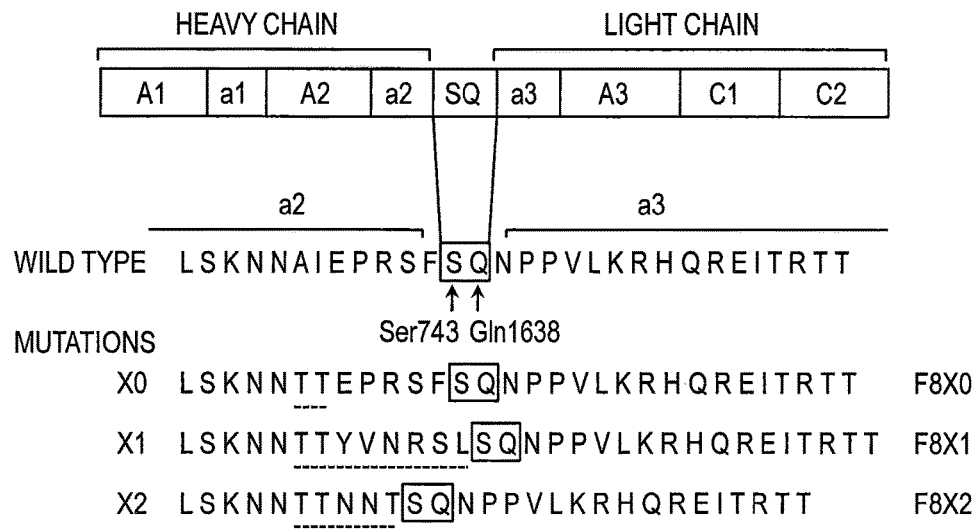
FIG. 8 shows the amino acid sequences of modified BDD FVIII proteins (SEQ ID NOS: 31-34). The SQ represents serine 743 (Ser 743) and glutamine (Gln 1638) at the junction of heavy chain and light chain of the BDD factor VIII (numbering based on SEQ ID NO: 5). The underlined letters highlight the mutated amino acids in the heavy chain.

Alternatively, we have replaced amino acids EPR at position 738-740 with NNT in mutant X0, resulting in two more glycosylation sites in mutant X2 (FIG. 8).

Example 4

Figure 9A:
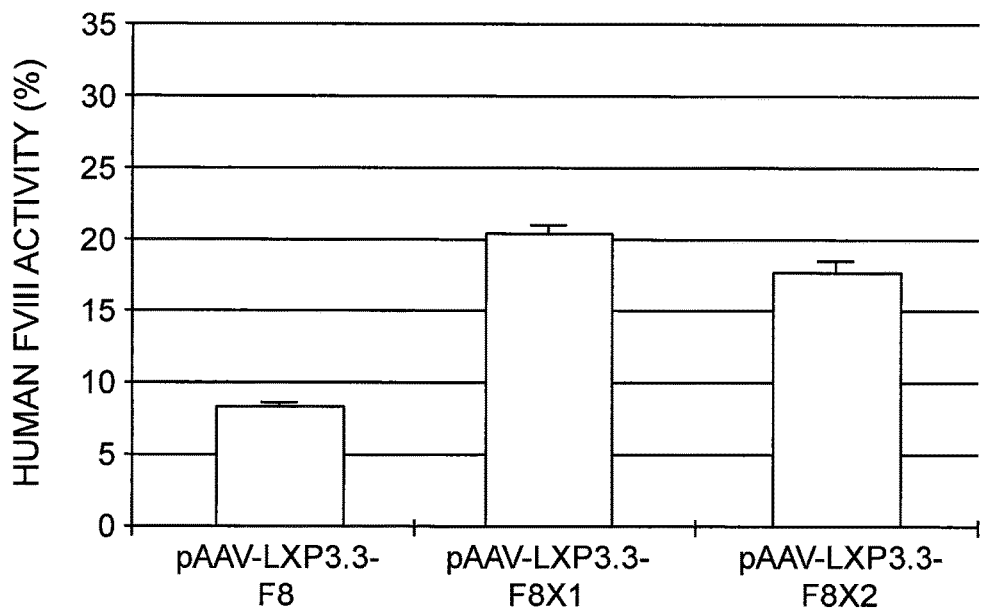
FIG. 9A shows human FVIII activity in Huh7 cells transfected with expression plasmids containing BDD Factor VIII or mutants F8X1 and F8X2 (see FIG. 8 for detail).

Mutations at the C-Terminus of Factor VIII Heavy Chain Enhanced FVIII Activities In Vitro We next compared the FVIII activities of the mutant constructs side by side with their wild type BDD FVIII counterpart. Transfection of the plasmids was carried out in human liver cancer cell line Huh7, which has no endogenous FVIII expression but is suitable for liver-specific promoter controlled gene expression. As shown in FIG. 9A, mutations X1 and X2 more than doubled the FVIII activities in vitro when compared to its parental gene.

Example 5

Figure 9B:
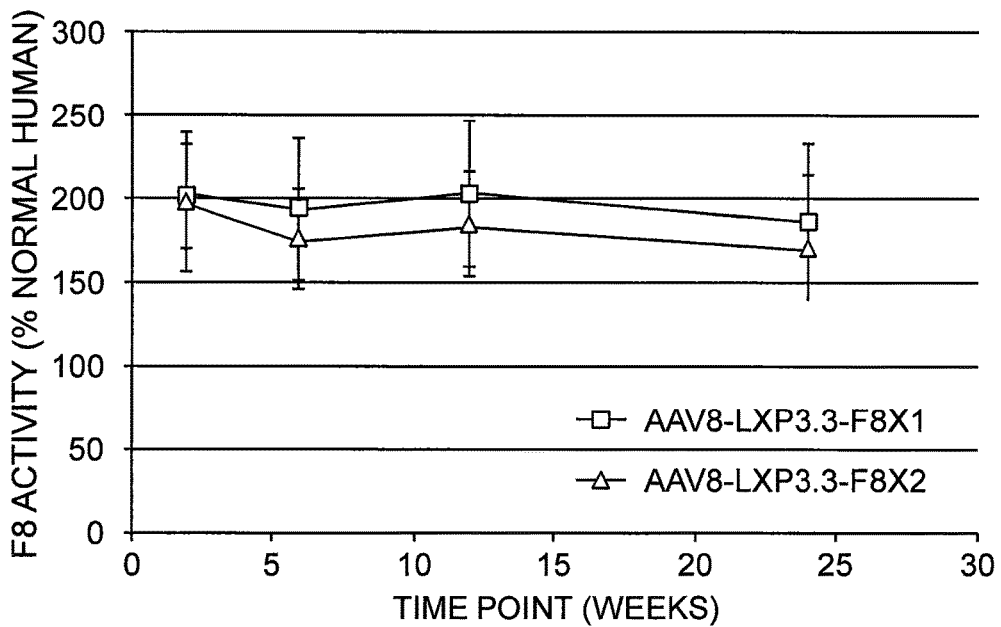
FIG. 9B shows AAV8 vector-mediated long-term expression of mutant human BDD FVIII genes in FVIII knockout mice. Human factor VIII activities (as percentage of normal human levels) were measured at various time points post intravenous injection of $5\times10^{10}$ vector genomes of AAV8-LXP3.3i-F8X1 or AAV8-LXP3.3i-F8X2.

Long-Term and High Level Gene Expression of the Mutant FVIII In Vivo in a Hemophilia A Mouse Model Since the FVIII mutants X1 and X2 showed significantly higher FVIII activities in the in vitro transfection experiments, we next examined their gene expression and FVIII activities in vivo in the FVIII KO mice. The X1 and X2 genes were under the transcriptional control of the same LXP3.3I promoter and packaged in AAV8 vector particles. Based on earlier experiments, a standard vector dose of $5 \times 10^{10}$ v.g./mouse was chosen and injected intravenously via the tail vein of the hemophilia A mice at the age of 2 to 3 months. Plasma samples were collected via the retroorbital bleeding technique, a commonly used method. As shown in FIG. 9B, both mutants X1 and X2 achieved higher expression than their wild-type parental BDD FVIII gene (compare to FIG. 7A, low dose). To monitor the long-term gene expression, we have kept hemophilia A mice that were treated with either the X1 or X2 mutants for observation for 24 weeks. Similar to the hemophilia A mice treated with the parental wt BDD FVIII vector (FIG. 7A), the mice treated with mutant FVIII vectors also showed long-term and stable gene expression without significant decrease of the human FVIII activities in the plasma. Inhibitor tests at various time points revealed no inhibitor formation.

It will be understood by those of skill in the art that numerous and various modifications can be made without departing from the spirit of the present invention. Therefore, it should be clearly understood that the forms of the present invention are illustrative only and are not intended to limit the scope of the present invention.

All publications, patent applications, patents, patent publications, sequences identified by GenBank® database accession numbers and other references cited herein are incorporated by reference in their entireties for the teachings relevant to the sentence and/or paragraph in which the reference is presented.

The foregoing is illustrative of the present invention, and is not to be construed as limiting thereof. The invention is defined by the following claims, with equivalents of the claims to be included therein.

Sequences:

SEQ ID NO: 1 LXP3.3 promoter—200 bp

SEQ ID NO: 2 (LXP3.3I containing LXP3.3 promoter and VH4 intron—288 bp

SEQ ID NO: 3 Synthetic human B-domain deleted factor FVIII coding sequence—4374 bp SEQ ID NO: 4 Human factor FVIII gene expression cassette in AAV vector, from left inverted repeat to right inverted terminal repeat—5045 bp SEQ ID NO: 5 Human factor FVIII wild-type protein sequence without signal peptide—2333 aa

What is claimed is:

1. An isolated polynucleotide comprising a synthetic liver specific promoter, wherein the promoter comprises the nucleotide sequence as set forth in SEQ ID NO: 1.

2. The polynucleotide of claim 1, wherein the promoter is operably linked to an intron.

3. The polynucleotide of claim 2, wherein the intron is from heavy chain variable region ($V_H$) 4 ($V_H4$).

4. The polynucleotide of claim 3, wherein the promoter and the intron together comprise the nucleotide sequence as set forth in SEQ ID NO: 2.

5. The polynucleotide of claim 1, wherein the promoter is operably linked to a polynucleotide of interest.

6. The polynucleotide of claim 5, wherein the polynucleotide of interest encodes a polypeptide or a functional nucleic acid.

7. The polynucleotide of claim 6, wherein the polynucleotide of interest encodes Factor VIII.

8. A vector comprising the polynucleotide of claim 1.

9. An isolated transformed cell comprising the polynucleotide of claim 1.

10. The polynucleotide of claim 6, wherein the polynucleotide of interest encodes a clotting factor.

11. The polynucleotide of claim 7, wherein the polynucleotide interest encodes a B domain-deleted Factor VIII.

12. The polynucleotide of claim 11, wherein the polynucleotide of interest comprises the nucleotide sequence as set forth in SEQ ID NO: 3.

13. The polynucleotide of claim 11, wherein the promoter and the polynucleotide of interest comprises the nucleotide sequence as set forth in SEQ ID NO: 4.

14. The polynucleotide of claim 1, further comprising a polyadenylation site downstream of the polynucleotide of interest.

15. The vector of claim 8, wherein the vector is a viral vector.

16. The vector of claim 14, wherein the vector is an adeno-associated virus vector.

* * * * *

UNITED STATES PATENT AND TRADEMARK OFFICE
CERTIFICATE OF CORRECTION

PATENT NO. : 10,308,705 B2
APPLICATION NO. : 15/017015
DATED : June 4, 2019
INVENTOR(S) : Xiao et al.

Page 1 of 1

It is certified that error appears in the above-identified patent and that said Letters Patent is hereby corrected as shown below:

In the Claims

Column 78, Line 27, Claim 16: delete "claim 14" and insert -- claim 15 --

Signed and Sealed this
Fifth Day of November, 2019

Andrei Iancu
*Director of the United States Patent and Trademark Office*